United States Patent
Christman et al.

(10) Patent No.: US 11,376,346 B2
(45) Date of Patent: Jul. 5, 2022

(54) EXTRACELLULAR MATRIX FOR TREATING PELVIC FLOOR DISORDERS AND SKELETAL MUSCLE DEGENERATION

(71) Applicant: The Regents of the University of California, Oakland, CA (US)

(72) Inventors: Karen Christman, San Diego, CA (US); Marianna Alperin, La Jolla, CA (US); Pamela Duran, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 59 days.

(21) Appl. No.: 16/612,511

(22) PCT Filed: May 16, 2018

(86) PCT No.: PCT/US2018/032866
§ 371 (c)(1),
(2) Date: Nov. 11, 2019

(87) PCT Pub. No.: WO2018/213375
PCT Pub. Date: Nov. 22, 2018

(65) Prior Publication Data
US 2020/0197567 A1   Jun. 25, 2020

Related U.S. Application Data

(60) Provisional application No. 62/507,850, filed on May 18, 2017.

(51) Int. Cl.
*A61L 27/36* (2006.01)
*A61L 27/58* (2006.01)

(52) U.S. Cl.
CPC ......... *A61L 27/3633* (2013.01); *A61L 27/367* (2013.01); *A61L 27/3683* (2013.01);
(Continued)

(58) Field of Classification Search
None
See application file for complete search history.

(56) References Cited

U.S. PATENT DOCUMENTS

2006/0293760 A1   12/2006   DeDeyne
2014/0178450 A1*   6/2014   Christman ........... A61K 9/0024
                                              424/422
(Continued)

FOREIGN PATENT DOCUMENTS

WO   WO-2015006436 A1 *   1/2015   ............. A61L 27/18

OTHER PUBLICATIONS

Proske, U., & Allen, T. J., Damage to Skeletal Muscle from Eccentric Exercise, Exerc. Sport Sci. Rev., 33 (2005) pp. 98-104. (Year: 2005).*

(Continued)

*Primary Examiner* — Dominic Lazaro
(74) *Attorney, Agent, or Firm* — Eversheds Sutherland (US) LLP

(57) ABSTRACT

Described herein are compositions comprising decellularized extracellular matrix derived from skeletal muscle or other suitable tissue, and therapeutic uses thereof. Methods for treating, repairing or regenerating defective, diseased, damage, ischemic, ulcer cells, tissues or organs in a subject preferably a human, with diseases associated with muscular degeneration, using a decellularized extracellular matrix of the invention are provided. Methods of preparing culture surfaces and culturing cells with absorbed decellularized extracellular matrix are provided.

9 Claims, 16 Drawing Sheets

(52) U.S. Cl.
CPC ........... *A61L 27/58* (2013.01); *A61L 2400/06* (2013.01); *A61L 2430/30* (2013.01)

(56) References Cited

U.S. PATENT DOCUMENTS

| | | |
|---|---|---|
| 2014/0242125 A1 | 8/2014 | Atala et al. |
| 2016/0213815 A1 | 7/2016 | Watschke |
| 2017/0087275 A1 | 3/2017 | Christman et al. |

OTHER PUBLICATIONS

Alperin, M., et al., Pregnancy-induced adaptations in intramuscular extracellular matrix of rat pelvic floor muscles, Am. J. Obstet. Gynecol., 215 (Aug. 2016) pp. 210. (Year: 2016).*

PCT International Search Report and Written Opinion for PCT Application No. PCT/US2018/032866 dated Jul. 30, 2018 (10 pages).

Alperin et al., "Pregnancy-Induced Adaptations in Intramuscular Extracellular Matrix of Rat Pelvic Floor Muscles," Am J Obstet Gynecol., 2016, 215(2):210.e1-210.e7.

Proske et al., "Damage to Skeletal Muscle from Eccentric Exercise," Exerc. Sport Sci. Rev., 2005, 33(2):98-104.

* cited by examiner

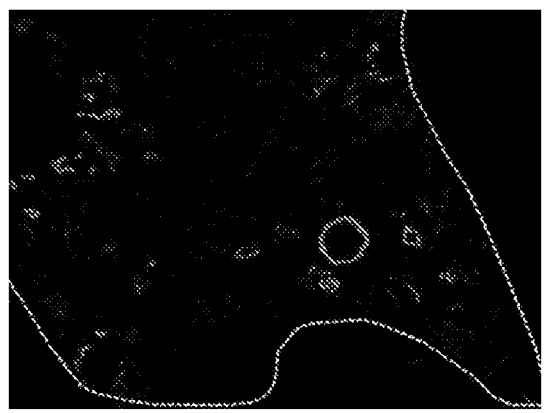
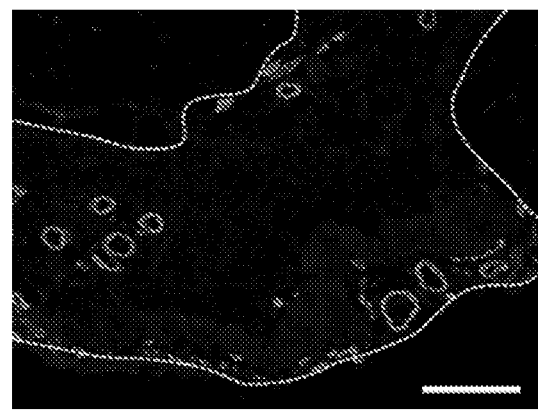
FIGURE 6AFIGURE 6B
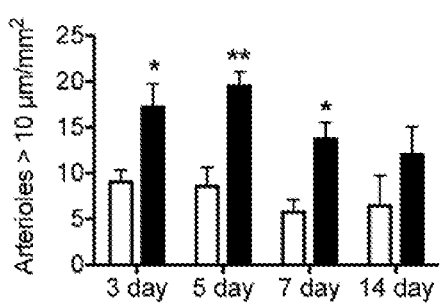
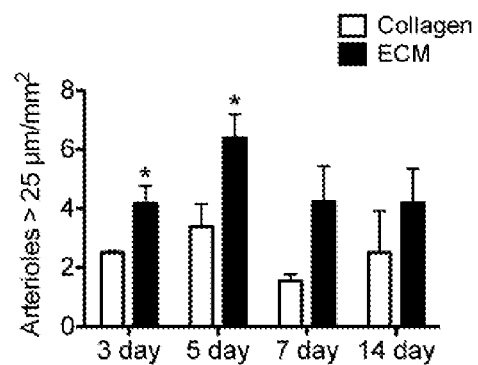
FIGURE 6CFIGURE 6D

EXTRACELLULAR MATRIX FOR TREATING PELVIC FLOOR DISORDERS AND SKELETAL MUSCLE DEGENERATION

CROSS REFERENCE TO RELATED APPLICATIONS

This application claims the priority benefit of PCT/US2018/032866 filed on May 16, 2018 which claims the priority benefit to U.S. Provisional Patent Application No. 62/507,850, filed May 18, 2017, the entire contents of which are incorporated by reference.

STATEMENT OF GOVERNMENT INTEREST

This invention was made with government support under Grant No. R01HL113468 awarded by National Institutes of Health (NIH). The government has certain rights in the invention.

BACKGROUND OF THE INVENTION

The extracellular matrix (ECM) of each tissue contains similar components; however, each individual tissue is composed of a unique combination of proteins and proteoglycans (Lutolf and Hubbell, 2005; Uriel et al., 2009). Recent studies have shown that the ECM of various tissues can be isolated through decellularization and utilized as a tissue engineering scaffold (Merritt et al.; Ott et al., 2008; Singelyn et al., 2009; Uygun et al., 2010; Valentin et al., 2010; Young et al., 2011). Other decellularized ECM materials have been used for a variety of applications for tissue repair (Crapo et al., 2011; Gilbert et al., 2006). These scaffolds are known to promote cellular influx in a variety of tissues (Numata et al., 2004; Rieder et al., 2006). Their degradation products have angiogenic (Li et al., 2004) and chemoattractant (Badylak et al., 2001; Beattie et al., 2008; Li et al., 2004; Zantop et al., 2006) properties, and also promote cell migration and proliferation (Reing et al., 2009). After removal of the cellular antigens, these scaffolds are considered biocompatible, and both allogeneic and xenogeneic ECM devices have been approved by the FDA and are in clinical use (Badylak, 2007).

Hydrogels derived from decellularized ECMs, including myocardium (Singelyn et al., 2009), pericardium (Seif-Naraghi et al., 2010), and adipose tissue (Young et al., 2011), were recently developed which assemble into porous and fibrous scaffolds upon injection in vivo. It has been shown that the injectable hydrogel derived from ventricular ECM promoted endogenous cardiomyocyte survival and preserved cardiac function post-myocardial infarction (Singelyn et al., 2012). ECM hydrogels have also been produced for treatment of ischemic muscle tissue due to peripheral artery disease and critical limb ischemia (See PCT/US2012/054058).

A liquid form of skeletal muscle matrix was shown to promote the differentiation and maturation of C2C12 skeletal myoblast progenitors when used as a cell culture coating due to its ability to retain a complex mixture of skeletal muscle ECM proteins, peptides, and proteoglycans (DeQuach et al., 2010). A decellularized skeletal muscle scaffold has been previously explored for replacement of a muscle defect (Merritt et al.; Wolf et al., 2012), yet this intact scaffold would not be amenable to treating certain non-skeletal muscle tissue disease, such as the peripheral artery disease (PAD) and CLI.

Skeletal muscles are composed of bundles of highly oriented and dense muscle fibers, each a multinucleated cell derived from myoblasts. The muscle fibers in native skeletal muscle are closely packed together in an extracellular three-dimensional matrix to form an organized tissue with high cell density and cellular orientation to generate longitudinal contraction. Skeletal muscle can become dysfunctional due to a variety of different factors including trauma, atrophy or degeneration.

The reconstruction of skeletal muscle, which is lost by injury, tumor resection, or various myopathies, is limited by the lack of functional substitutes. Surgical treatments, such as muscle transplantation and transposition techniques, have had some success; however, there still exists a need for alternative therapies. Tissue engineering approaches offer potential new solutions; however, current options offer incomplete regeneration. Many naturally derived as well as synthetic materials have been explored as scaffolds for skeletal tissue engineering, but none offer a complex mimic of the native skeletal extracellular matrix, which possesses important cues for cell survival, differentiation, and migration.

The extracellular matrix consists of a complex tissue-specific network of proteins and polysaccharides, which help regulate cell growth, survival and differentiation. Despite the complex nature of native ECM, in vitro cell studies traditionally assess cell behavior on single ECM component coatings, thus posing limitations on translating findings from in vitro cell studies to the in vivo setting. Overcoming this limitation is important for cell-mediated therapies, which rely on cultured and expanded cells retaining native cell behavior over time.

Typically, purified matrix proteins from various animal sources are adsorbed to cell culture substrates to provide a protein substrate for cell attachment and to modify cellular behavior. However, these approaches would not provide an accurate representation of the complex microenvironment. More complex coatings have been used, such as a combination of single proteins, and while these combinatorial signals have shown to affect cell behavior, it is not as complete as in vivo. For a more natural matrix, cell-derived matrices have been used. Matrigel is a complex system; however, it is derived from mouse sarcoma, and does not mimic any natural tissue. While many components of ECM are similar, each tissue or organ has a unique composition, and a tissue specific naturally derived source may prove to be a better mimic of the cell microenvironment.

Pelvic Floor Disorders (PFD)

Pelvic floor disorders (PFD), which include urinary (UI) and fecal incontinence (FI), and pelvic organ prolapse (POP), are debilitating conditions that affect a quarter of the U.S. female population. The prevalence of UI, which is the most common PFD, is 17%, followed by H with 9-15% prevalence, and POP with 3% prevalence rate. By 2050, the number of women with PFD is predicted to increase to 43.8 million. Maternal birth trauma and consequent dysfunction of urethral sphincter (US), external anal sphincter (EAS) and pelvic floor (PFM) skeletal muscles, is a leading risk factor for UI, H, and POP, respectively. Currently, there are no preventive measures, beyond Cesarean section, and the existing treatments are associated with significant morbidities, while offering marginal promise at best.

Focal Skeletal Muscle Degeneration

Dysfunction of striated muscles, which include the rotator cuff muscles (supraspinatus, infraspinatus, teres minor, subcapularis), hip abductor muscle (gluteus medius, gluteus minimus, gluteus maximus, and short external rotators), foot and ankle muscles (tibialis posterior, gastrocnemius, soleus), lumbar spine muscles (multifidus, erector spinae), and knee extensor muscles (quadriceps), all suffer from fatty atrophy and muscle degeneration as a consequence of chronic joint disease and other neuromuscular pathologies. This loss of muscle interferes with muscle and joint function, which negatively impacts quality of life.

SUMMARY OF THE INVENTION

The primary therapeutic goal in female pelvic medicine is to restore normal pelvic floor function. Despite this, the current standard treatments are compensatory, as they do not directly target sphincteric and supportive muscle dysfunction and do not reverse the existing injury or halt functional deterioration. In contrast, the present invention provides a novel injectable biomaterial scaffold, derived from decellularized skeletal muscle extracellular matrix (ECM), which capitalizes on the endogenous regenerative potential of the host tissue and bridges this therapeutic void by restoring and preserving function of injured pelvic muscles and striated focal skeletal muscles.

In embodiments the invention provides an injectable biomaterial scaffold and a minimally invasive delivery system for the treatment of US, EAS, and PFM. Upon injection, the material will set up into a porous and fibrous scaffold that will facilitate endogenous cell infiltration to regenerate and heal the damaged muscles post-vaginal delivery thereby preventing the development of PFD.

The present invention provides a new use for ECM materials that have already shown to promote differentiation of muscle progenitors in vitro (DeQuach et al., *PLoS One*, 2010), as well as migration of muscle progenitors, decrease in cell death, and increase in neovascularization and muscle development in vivo in hindlimb ischemia models of muscle damage (DeQuach et al., *ECM*, 2012; Ungerleider, et al., *JACC: BTS*, 2016). This approach has significant clinical application as injectable scaffolds can be delivered with minimal invasiveness, thereby enabling their administration in labor and delivery units and outpatient settings, and reducing patient recovery time and perioperative morbidity compared to surgical approaches. This biomaterials based approach is also likely to reach the clinic sooner as it is devoid of the hurdles related to stem-cell based therapies and obviates the difficulties and expense associated with administration of exogenous growth factors. In fact, the analogous hydrogel derived from decellularized porcine myocardium is already in clinical trials for myocardial repair and is two orders of magnitude cheaper to manufacture compared to cell products. In addition, stem cell based therapies suffer from poor cell survival and have led to increased connective tissue rather than muscle regeneration in urethral sphincter (Sadeghi, et al. *Int Urogynecol J*, 2016).

Importantly, application of the injectable skeletal muscle matrix scaffold to treat pelvic muscles, injured during vaginal delivery, can shift the current clinical paradigm towards prevention of postpartum muscle dysfunction, which is essential for meaningful advances to occur in female pelvic medicine. Ultimately, this innovative approach will reduce the incidence of PFD and improve the lives of millions of women.

Presently, postpartum pelvic floor muscle dysfunction is thought to be due to radiologically detected muscle tears or avulsions, which have been the primary focus of the literature to date. Morgan D M, Larson K, Lewicky-Gaupp C, Fenner D E, DeLancey J O 2011 Vaginal support as determined by levator ani defect status 6 weeks after primary surgery for pelvic organ prolapse. *Int J Gynaecol Obstet* 114:141-144; Kearney R, Fitzpatrick M, Brennan S, Behan M, Miller J, Keane D, O'Herlihy C, DeLancey J O L 2010 Levator ani injury in primiparous women with forceps delivery for fetal distress, forceps for second stage arrest, and spontaneous delivery. *International journal of gynaecology and obstetrics* 111:19-22; DeLancey J O, Kearney R, Chou Q, Speights S, Binno S 2003 The appearance of levator ani muscle abnormalities in magnetic resonance images after vaginal delivery. *Obstet Gynecol* 101:46-53; Dietz H P, Lanzarone V 2005 Levator trauma after vaginal delivery. *Obstet Gynecol* 106:707-712.

The present invention provides that direct measures of pelvic floor muscle properties indicate that strains imposed on the pelvic floor muscles (PFMs) during simulated birth injury (SBI) result in acute sarcomere hyperelongation and myofibrillar disruption, not avulsions (FIGS. 13A-13B and 14A-14B). These acute events lead to PFM fibrosis, similar to the degenerative changes observed in human PFMs, as well as functional alterations. However, the population of resident muscle progenitors (satellite cells) appears to be normal. This suggests that viable cells are present in PFMs, but are not able to mount a response sufficient for regeneration after birth injury. One would not expect to be able to repair what was believed to be a torn muscle (i.e., an avulsion) with an injectable ECM hydrogel material.

The existing knowledge regarding the impact of aging on PFMs is mainly derived from conventional radiological examinations that are compromised by low resolution. These imaging studies use volumetric measures, such as muscle cross-sectional area, and have failed to identify age-related atrophy in PFMs, due to their inability to distinguish between, and identify changes in, contractile vs. ECM components. Morris V C, Murray M P, Delancey J O, Ashton-Miller J A 2012 A comparison of the effect of age on levator ani and obturator internus muscle cross-sectional areas and volumes in nulliparous women. *Neurourol Urodyn* 31:481-486.

Employing experimental tools, not previously utilized in female pelvic medicine, the present invention determined that physiological alterations, such as decrease in force production and excursion, as well as degenerative changes, such as fibrosis, occur in aged PFMs. These novel tissue-level findings provide a mechanistic link between aging and PFM dysfunction and serve as an impetus for providing preventative strategies to mitigate the untoward aging effects. Furthermore, identification of substantial fibrosis in aged PFMs provides novel treatment approaches, aimed at reversing functionally relevant pathological changes by promoting muscle regeneration. Alperin M, Cook M S, Tuttle L I, Esparza M, Lieber R L. Impact of vaginal parity and aging on the architectural design of pelvic floor muscles. *Am J Obstet Gynecol*. 2016 September; 215(3):312.e.1-9. PAM: 26953079 PMCID: 5003683; Cook M S, Bou-Malham L, Esparza M C, Alperin M. Age-related alterations in obturator internus muscle. *Int Urogynecol J*. 2016 Oct. 4. [Epub ahead of print] MUD: 27704154.

Furthermore, urinary and anal sphincters are thin circular muscles, which are very different types of muscles than previously targeted for ECM hydrogel or patch administration.

The present invention provides biomaterials comprising extracellular matrix (ECM) derived from skeletal muscle or other suitable tissue, and method of use thereof, for therapeutic treatment of skeletal muscle degeneration. The invention provides for the treatment of acute sarcomere hyperelongation and myofibrillar disruption, rather than avulsions. The invention provides for the treatment of PFM fibrosis and other pelvic floor disorders (PFD), which include urinary (UI) and fecal incontinence (FI), and pelvic organ prolapse (POP), and/or other muscular diseases. In embodiments, the targeted muscle tissue includes urinary and anal sphincters. The invention provides for the treatment of dysfunction of pelvic striated muscles, which include external urethral (EUS) and external anal (EAS) sphincteric muscles, and pelvic floor muscles (PFM). The invention provides for the treatment of patients with Rectal Prolapse (RP), Stress Urinary Incontinence (SUI), Mixed Urinary Incontinence (MUI), SUI/MUI, patients with SUI/MUI and intrinsic sphincter deficiency, patients with SUI/MUI and pelvic floor muscle (PFM) dysfunction, and vaginally parous women.

With respect to orthopedic application, the invention provides for the treatment of degenerative muscle conditions which are also not avascular ischemic type injuries. Here there is accelerated apoptosis in such tissues, and the prior art has attempted to replace cells as a treatment. The present invention provides, however, a unique pathology showing that a skeletal muscle ECM hydrogel can improve muscle degeneration.

In certain embodiments, the present invention provides injectable biomaterials comprising skeletal muscle extracellular matrix, and method of use thereof, for treating orthopedic diseases, and symptoms and associated complications with these diseases. Orthopedic conditions resulting from skeletal muscle degenerative disease contemplated for treatment by the present invention include dysfunction of striated muscles, which include the rotator cuff muscles (supraspinatus, infraspinatus, teres minor, subcapularis), hip abductor muscle (gluteus medius, gluteus minimus, gluteus maximus, and short external rotators), foot and ankle muscles (tibialis posterior, gastrocnemius, soleus), lumbar spine muscles (multifidus, erector spinae), and knee extensor muscles (quadriceps). Patients in need may suffer from fatty atrophy and muscle degeneration as a consequence of chronic joint disease and other neuromuscular pathologies. This loss of muscle interferes with muscle and joint function, which negatively impacts quality of life. The invention provides for the treatment of shoulder, hip, foot and ankle, lumbar spine, and knee degenerative joint and tendon diseases, which are associated with focal muscle atrophy and degeneration. Patients in need include those with tendinopathy and/or tendon rupture, patients with osteoarthritis, patients with rheumatoid arthritis, and patients with lower back pain for example.

In certain embodiments, the present invention provides compositions and methods comprising injecting or implanting in a subject in need an effective amount of a composition comprising decellularized extracellular matrix derived from skeletal muscle tissue. In other embodiments, the present invention provides a method comprising injecting or implanting in a subject in need a composition comprising decellularized extracellular matrix derived from a suitable tissue, including but not limited to, cardiac, pericardial, liver, brain, small intestine submucosa, bladder, and vascular tissue. In certain embodiments, the injection or implantation of said composition repairs damage to skeletal muscle tissue sustained by said subject. In other embodiments, the injection or implantation of said composition repairs damage caused by muscular degeneration in said subject.

The composition of the present invention comprising the ECM material can degrade within about one month, two months, or three months following injection or implantation. In certain embodiments, the injection or implantation of said composition repairs damage to skeletal muscle tissue sustained by said subject. In certain embodiments, the injection or implantation of said composition repairs damage caused by muscular degeneration in said subject. Herein, said effective amount can be an amount that increases blood flow in the area of the injection or implantation or treated limb of the treated subject. In some instances, the effective amount is an amount that induces new vascular formation in the area of the injection or implantation of the treated subject. The present invention provides that a liquid form of skeletal muscle matrix can assemble into a fibrous scaffold upon injection in vivo. The material can also be processed into a lyophilized form that only requires sterile water, PBS, or saline to re-suspend prior to injection, which can provide ease of storage and use in a clinical setting. The composition can further comprise cells, drugs, proteins, or polysaccharides. In some instances, the composition is coated on a device such as an implant. The composition can be delivered as a liquid, and in many instances, the composition can transition to a gel form after delivery. In certain embodiments, the composition is delivered as a powder.

In one aspect, the invention provides a composition comprising decellularized extracellular matrix derived from skeletal muscle tissue or other suitable tissues. The composition can be injectable. The composition can be formulated into a powder or particulate. In other instances, the composition can be formulated to be in liquid form at room temperature, typically 20° C. to 25° C., and in gel form at a temperature greater than room temperature or greater than 35° C. In some instances, the composition is configured to be delivered to a tissue parenterally, such as through a small gauge needle (e.g., 27 gauge or smaller). In some instances, said composition is suitable for direct implantation into a patient. The composition can be formulated either in a dry or hydrated form to be placed on or in wounds.

In some instances the composition comprises native proteins. In some instances the composition comprises native peptides. In some instances the composition comprises native glycosaminoglycans. In some instances, the composition further comprises non-naturally occurring factors that recruit cells into the composition, encourage growth or prevent infection. In some embodiments, the composition comprising decellularized extracellular matrix derived from skeletal muscle tissue herein retains native glycosaminoglycans. In some instances, the composition comprises naturally occurring factors that recruit cells into the composition, encourage growth or prevent infection.

In some instances, the composition further comprises a population of exogenous or autologous therapeutic cells. The cells can be stem cells or other precursors of skeletal muscle cells or other cell types.

In some instances, the composition further comprises a therapeutic agent, and as such is configured as a drug delivery vehicle. In some instances, the composition is configured to coat surfaces, such as tissue culture plates or scaffolds, to culture skeletal muscle, skeletal muscle cells, or other cell types relevant to skeletal muscle repair.

In an aspect, a method of producing a composition is disclosed herein that comprises decellularized skeletal muscle or other tissue extracellular matrix comprising: obtaining from a subject a skeletal muscle or other suitable tissue sample having an extracellular matrix and non-extracellular matrix components; processing skeletal muscle or other tissue sample to remove the non-extracellular matrix component to obtain decellularized skeletal muscle or other tissue extracellular matrix and extracellular proteins and polysaccharides; and sterilizing the decellularized skeletal muscle or other tissue extracellular matrix. In some instances, said method is performed aseptically without sterilization. In some instances, said method further comprises the step of lyophilizing and grinding up the decellularized skeletal muscle or other tissue extracellular matrix. In some instances, said method further comprises the step of enzymatically treating, solubilizing, or suspending the decellularized skeletal muscle or other tissue extracellular matrix. In some instances, said decellularized skeletal muscle or other tissue extracellular matrix is digested with pepsin at a low pH.

In some instances, said method further comprises the step of suspending and neutralizing said decellularized skeletal muscle or other tissue extracellular matrix in a solution. In some instances, said solution is a phosphate buffered solution (PBS) or saline solution which can be injected through a high gauge needle into the desired tissue or organ. In some instances, said composition is formed into a gel at body temperature. In some instances, said composition further comprises cells, drugs, proteins or other therapeutic agents that can be delivered within or attached to the composition before, during or after gelation.

In some instances, said solution is placed into tissue culture plates or wells, incubated at above 35° C. or about 37° C. to form into a gel that is used for cell culture. In one aspect, the invention provides a method of culturing cells on an adsorbed matrix comprising the steps of: providing a solution comprising decellularized extracellular matrix derived from skeletal muscle or other suitable tissues into a tissue culture device; incubating said tissue culture plates device; removing said solution; and culturing cells on the adsorbed matrix. In some instances, said cells are skeletal muscle cells or other cell types relevant to skeletal muscle or other tissue repair.

In an aspect, a method of culturing cells on an adsorbed matrix comprises the steps of: providing a solution comprising decellularized extracellular matrix derived from skeletal muscle or other suitable tissues into a tissue culture device; incubating said tissue culture plates device; removing said solution; and culturing cells on the adsorbed matrix. In some instances, said cells are skeletal myoblasts, stem cells or other cell types relevant to skeletal muscle repair.

In one aspect, the invention provides a therapeutic method for skeletal muscle and/or other tissue (such as ischemic tissue, or ulcer tissue) repair in a subject comprising injecting or implanting a therapeutically effective amount of a composition comprising decellularized extracellular matrix derived from skeletal muscle or other suitable tissue into a subject in need thereof. In an aspect, a therapeutic method for skeletal muscle or other tissue repair in a subject comprises implanting a composition comprising decellularized extracellular matrix derived from skeletal muscle or other suitable tissues.

BRIEF DESCRIPTION OF THE DRAWINGS

FIG. 1A shows decellularized skeletal muscle matrix. FIG. 1B shows lyophilized skeletal muscle matrix prior to milling. FIG. 1C shows digested skeletal muscle matrix. FIG. 1D shows in vitro gel of the skeletal muscle matrix with media on top in right well. FIG. 1E shows that skeletal muscle matrix that has been digested and re-lyophilized FIG. 1F shows re-lyophilized skeletal muscle matrix resuspended using only sterile water.

FIG. 2A shows rat aortic smooth muscle cells and FIG. 2B shows that C2C12 skeletal myoblasts were cultured using growth media with the addition of degraded skeletal muscle matrix, collagen, or pepsin. Proliferation rate was increased for both cell types when cultured in the presence of skeletal muscle matrix degradation products.

FIG. 4A shows intramuscular injection of the skeletal muscle matrix material. FIG. 4B shows gelation of the skeletal muscle matrix in situ after 20 minutes as seen after excision of the muscle; arrow denotes the white matrix. FIG. 4C shows DAB staining of the biotin-labeled skeletal muscle matrix that gelled within the muscle. Scale bar at 200 µm.

FIGS. 6A-6D illustrate quantification of arterioles. FIG. 6A shows collagen and FIG. 6B shows skeletal muscle matrix injection regions stained with anti-alpha-SMA (red greyscale) to determine arteriole formation. Vessels with a clear lumen are seen within the injection region at 5 days. Scale bar at 100 µm. Quantification of the vessel density at 3, 5, 7, and 14 days for vessels with a lumen FIG. 6C >10 µm or FIG. 6D >25 µm demonstrated that the skeletal muscle matrix increased neovascularization. Vessels were, on average, larger in the skeletal muscle matrix when compared to collagen.

FIG. 7A shows collagen and FIG. 7B shows skeletal muscle matrix injection regions stained with isolectin (green greyscale) to assess endothelial cell infiltration at 5 days. Scale bar at 100 µm. * and dotted line denote area of material. FIG. 7C shows that endothelial cell infiltration at 3, 5, 7, and 14 days was similar across all four time points, but was significantly greater in the skeletal muscle matrix injection region at 3 and 7 days post-injection.

FIG. 8A shows collagen injection region and FIG. 8B shows skeletal muscle matrix injection region at 5 days with desmin-stained cells (green greyscale) co-labeled with Ki67 (red greyscale). Arrows denote desmin and Ki67 positive cells. Scale bar at 20 µm. Insert shows positive desmin staining of healthy skeletal muscle, scale bar at 100 µm. FIG. 8C shows quantification of desmin-positive cells in the skeletal muscle matrix compared to collagen normalized to area. Note that there are significantly more desmin-positive cells in the skeletal muscle matrix. FIG. 8D shows that, of these desmin-positive cells, a majority of the cells are proliferating as seen by Ki67 co-labeling.

FIG. 9C shows graph of MyoD-positive cells normalized to the area for the injection region. The number of MyoD-positive cells was significantly higher in the skeletal muscle matrix regions at all time points.

FIG. 10A shows a gross image of rabbit supraspinatus muscle following intramuscular injection of the skeletal muscle matrix material. FIG. 10B shows Hematoxylin and Eosin staining of rabbit supraspinatus muscle cross sections demonstrating the gelation of the gelation of the skeletal muscle matrix in situ. Arrows denote the gelled white matrix within the muscle. Scale bar at 500 µm.

FIG. 11A shows a proximal section of iliococcygeus muscle following intramuscular injection of the skeletal muscle matrix material. FIG. 11B shows a proximal section of pubococcygeus following intramuscular injection of the skeletal muscle matrix material. Arrows denote the gelled white matrix prelabeled with Alexa Fluor 568. Green (laminin) Scale bar at 500 µm.

FIG. 13A shows uninjured control. FIG. 13B shows the departure from normal muscle appearance following simulated birth injury, indicated by misalignment and smearing of sarcomeres. Scale bar at 1 µm.

FIG. 14A shows uninjured control. FIG. 14B shows the departure from normal muscle appearance following simulated birth injury, indicated by misalignment and smearing of sarcomeres. Scale bar at 2 µm. Adapted from Catanzarite, et al. AM J Obstet Gynecol (2018). 218:5.

DETAILED DESCRIPTION OF THE INVENTION

Figure 1A:
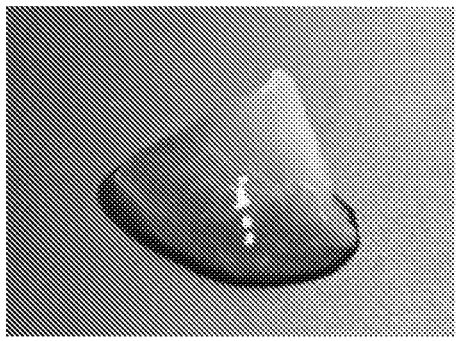
FIGS. 1A-1F illustrate decellularization and tissue processing.

The present invention provides a decellularized skeletal muscle extracellular matrix (ECM) composition, and method of use thereof, for preventing and treating muscle degeneration and other tissue damage, as well as for restoring muscle mass and function in certain diseases. Described herein are compositions comprising ECM derived from skeletal muscle tissue or other suitable tissues, including, but not limited to, cardiac, pericardial, liver, brain, small intestine submucosa, bladder, and vascular tissue, which can be used for injection into skeletal muscle tissue and/or other tissues in need of therapeutic treatment. In certain embodiments, the ECM composition of the present invention can also be used to support injured tissue or change the mechanical properties. In certain embodiments, the ECM composition as described herein can help regenerate defective or absent skeletal muscle and restore muscle mass and function. In certain embodiments, the injection or implantation of said composition repairs damage to skeletal muscle tissue sustained by said subject.

In certain embodiments, the present invention provides a decellularized skeletal muscle extracellular matrix (ECM) composition, and method of use thereof, for treating acute sarcomere hyperelongation and myofibrillar disruption. The invention provides for the treatment of PFM fibrosis and other pelvic floor disorders (PFD), which include urinary (UI) and fecal incontinence (FI), and pelvic organ prolapse (POP), and/or other muscular diseases. In embodiments, the targeted muscle tissue includes urinary and anal sphincters. The invention provides for the treatment of dysfunction of pelvic striated muscles, which include external urethral (EUS) and external anal (EAS) sphincteric muscles, and pelvic floor muscles (PFM). The invention provides for the treatment of patients with Rectal Prolapse (RP), Stress Urinary Incontinence (SUI), Mixed Urinary Incontinence (MUI), SUI/MUI, patients with SUI/MUI and intrinsic sphincter deficiency, patients with SUI/MUI and pelvic floor muscle (PFM) dysfunction, and vaginally parous women.

The invention provides for the prevention and treatment of degenerative muscle conditions associated with orthopedic disease. In certain embodiments, the present invention provides therapeutic biomaterials comprising skeletal muscle extracellular matrix, and method of use thereof, for treating orthopedic diseases, and symptoms and associated complications with these diseases. Orthopedic conditions resulting from skeletal muscle degenerative disease contemplated for treatment by the present invention include dysfunction of striated muscles, which include the rotator cuff muscles (supraspinatus, infraspinatus, teres minor, subcapularis), hip abductor muscle (gluteus medius, gluteus minimus, gluteus maximus, and short external rotators), foot and ankle muscles (tibialis posterior, gastrocnemius, soleus), lumbar spine muscles (multifidus, erector spinae), and knee extensor muscles (quadriceps). Patients in need may suffer from fatty atrophy and muscle degeneration as a consequence of chronic joint disease and other neuromuscular pathologies. This loss of muscle interferes with muscle and joint function, which negatively impacts quality of life. The invention provides for the treatment of shoulder, hip, foot and ankle, lumbar spine, and knee degenerative joint and tendon diseases, which are associated with focal muscle atrophy and degeneration. Patients in need include those with tendinopathy and/or tendon rupture, patients with osteoarthritis, patients with rheumatoid arthritis, and patients with lower back pain for example.

The present invention further provides a method of delivering the decellularized skeletal muscle extracellular matrix (ECM) composition of the present invention, with or without other therapeutic agents, including cells, into one or more injured tissues or organs damaged by certain disease conditions or trauma. In some instances, methods of delivery are described wherein the skeletal muscle ECM composition of the present invention can be placed in contact with a defective, diseased or absent muscle tissues or other injured tissues, resulting in skeletal muscle tissue regeneration and restoration of muscle mass and function. Exemplary methods for delivery of a composition comprising the skeletal muscle ECM include, but are not limited to: direct instillation during surgery; direct injection into the injured tissue or organ; indirect delivery through a catheter to the injured tissue or organ. The composition can also be delivered as a liquid, gel or in a solid formulation, such as a graft or patch or associated with a cellular scaffold or a particulate. Dosages and frequency will vary depending upon the needs of the patient and judgment of the physician.

In certain embodiments, the present invention provides a native skeletal muscle ECM decellularization and gelation method to create an in situ scaffold for cellular transplantation. An appropriate digestion and preparation protocol has been provided herein that can create nanofibrous gels. The gel solution is capable of being parenterally delivered into the skeletal muscle tissue or other injured tissue or organ, thus providing an in situ gelling scaffold. Since a decellularized skeletal muscle ECM best mimics the natural skeletal muscle environment, it improves cell survival and retention upon injection at the site of the injured tissue, thus encouraging tissue regeneration.

The skeletal muscle ECM of the present invention can also be used to recruit cells into the injured tissue or as a drug delivery vehicle. In some instances, the composition herein can recruit endogenous cells within the recipient and can coordinate the function of the newly recruited or added cells, allowing for cell proliferation or migration within the composition. An extracellular matrix composition herein can further comprise one or more additional components, for example without limitation: an exogenous cell, a peptide, polypeptide, or protein, a vector expressing a DNA of a bioactive molecule, and other therapeutic agents such as drugs, cellular growth factors, nutrients, antibiotics or other bioactive molecules. Therefore, in certain preferred embodiments, the ECM composition can further comprise an exogenous population of cells such as stem cells or progenitor, or skeletal muscle cell precursors, as described below.

The skeletal muscle ECM of the present invention can be derived from the native or natural matrix of mammalian skeletal muscle tissue. The skeletal muscle ECM of the present invention can also be derived from an animal or synthetic source. In some instances, the decellularized skeletal muscle extracellular matrix is derived from native skeletal muscle tissue selected from the group consisting of human, porcine, bovine, goat, mouse, rat, rabbit, or any other mammalian or animal skeletal muscle. In some embodiments, the biocompatible composition comprising the decellularized skeletal muscle extracellular matrix is in an injectable gel or solution form, and can be used for skeletal muscle or other tissue repair by transplanting or delivering cells contained therein into the injured or desired tissue in need following a disease condition, or recruiting the patient's own cells into the injured or desired tissue in need. In other instances, the biocompatible material comprising a decellularized skeletal ECM is, for example, a patch, an emulsion, a viscous liquid, fragments, particles, microbeads, or nanobeads.

In some instances, the invention provides biocompatible materials for culturing skeletal muscle cells or other skeletal muscle relevant cells in research laboratories, or in a clinical setting prior to transplantation and for skeletal muscle or other tissue repair. Methods for manufacturing and coating a surface, such as tissue culture plates or wells, with decellularized skeletal extracellular matrix are also provided. The biocompatible materials of the invention are also suitable for implantation into a patient, whether human or animal.

The invention further provides a method of producing a biocompatible material comprising the decellularized skeletal muscle extracellular matrix of the invention. Such method comprises the steps of: (a) obtaining a skeletal muscle tissue sample having an extracellular matrix component and non-extracellular matrix component; (b) processing the skeletal muscle tissue sample to remove at least a portion or substantially all the non-extracellular matrix component to obtain decellularized skeletal muscle extracellular matrix; and (c) sterilizing the decellularized skeletal muscle extracellular matrix. In certain embodiments, the skeletal muscle tissue sample is isolated from a mammal such as a non-primate (e.g., cows, pigs, horses, cats, dogs, rats, etc.) or a primate (e.g., monkey and human), or an avian source (e.g., chicken, duck, etc.). Decellularization procedures for the skeletal tissue sample are performed using one or more physical, chemical and/or biological techniques, known in the art and as taught herein. Methods of making the compositions herein can include decellularizing tissue from any age animal or human by methods well known in the art.

For human therapy, there are many potential sources for the skeletal muscle extracellular matrix material: human skeletal muscle (including autologous, allogeneic, or cadaveric), porcine skeletal muscle, bovine skeletal muscle, goat skeletal muscle, mouse skeletal muscle, rat skeletal muscle, rabbit skeletal muscle, chicken skeletal muscle, and other animal sources. One donor skeletal muscle can be used to treat many people. Non-human animals are a source of skeletal muscle extracellular matrix without the need for human donors. As a research reagent, non-human animal sources can be utilized.

In certain embodiments, the method of processing the skeletal muscle extracellular matrix is as follows. The skeletal tissue is first decellularized, leaving only the extracellular matrix. Decellularization can be performed with a perfusion of sodium dodecyl sulfate and phosphate buffered solution, or other detergents, for example. The skeletal muscle extracellular matrix is then lyophilized, ground up, and digested with pepsin at a low pH, between about pH 1-6 or pH 1-4, or other matrix degrading enzymes such as matrix metalloproteinases.

To produce a gel form of the skeletal muscle extracellular matrix for in vivo therapy, the solution comprising the skeletal muscle extracellular matrix is then neutralized and brought up to the desired temperature, concentration and viscosity using PBS/saline. In certain embodiments, the ECM concentration can be 1-20 mg/mL, or 2-8 mg/mL. The solution comprising the skeletal muscle extracellular matrix can then be injected through a high gauge needle, such as 27 gauge or higher, into the injured tissue or any tissue in need. At body temperature, e.g., 36.8° C.±0.7° C., such solution then forms into a gel. Cells, drugs, proteins, or other therapeutic agents can also be delivered inside the skeletal muscle ECM gel.

To produce a gel form of the skeletal muscle extracellular matrix for in vitro uses, the solution comprising the skeletal muscle extracellular matrix is neutralized and brought up to the desired concentration using PBS/saline. In certain embodiments, the ECM concentration can be 1-20 mg/mL, or 2-8 mg/mL. Such solution can then be placed onto any solid surface such as into tissue culture plates/wells. Once placed in an incubator at 37° C. or above room temperature, the solution forms a gel that can be used for cell culture.

The invention also provides a therapeutic method for skeletal muscle or other relevant tissue repair in a subject comprising injecting or implanting in part or in its entirety the biocompatible skeletal muscle ECM material of the invention into a patient. The invention further provides a therapeutic method for preventing or treating degenerative muscles or other defective, diseased, damaged, or injured tissue or organ in a subject comprising injecting or implanting the biocompatible material of the invention in situ.

The compositions herein can comprise a decellularized ECM derived from skeletal muscle tissue and another component or components. In some instances, the amount of ECM in the total composition is greater than 90% or 95% or 99% of the composition by weight. In some embodiments, the ECM in the total composition is greater than 1%, 5%, 10%, 20%, 30%, 40%, 50%, 60%, 70%, or 80% of the composition by weight.

Decellularized extracellular matrices are prepared such that much of the bioactivity for skeletal muscle tissue regeneration is preserved. Exemplary bioactivity of the compositions herein include without limitation: control or initiation of cell adhesion, cell migration, cell differentiation, cell maturation, cell organization, cell proliferation, cell death (apoptosis), stimulation of angiogenesis, proteolytic activity, enzymatic activity, cell motility, protein and cell modulation, activation of transcriptional events, provision for translation events, inhibition of some bioactivities, for example inhibition of coagulation, stem cell attraction, chemotaxis, and MMP or other enzyme activity.

The compositions comprise an extracellular matrix that is substantially decellularized. In some instances, a decellularized matrix comprises no living native cells with which the ECM naturally occurs. In some instances, a substantially decellularized matrix comprises less than 1%, 2%, 3%, 4%, 5%, 6%, 7%, 8%, 9% or 10% native cells by weight.

As described herein, a composition can comprise a decellularized skeletal muscle ECM and different tissue decellularized EMC or a synthetic or naturally occurring polymer from animal and non-animal sources (such as plants or synthetic collagens). For example, a composition herein comprises a natural polymer such as collagen, chitosan, alginate, glycosaminoglycans, fibrin, or hyaluronic acid. In another example, a composition herein comprises a synthetic polymer, for example without limitation, polyethylene glycol, poly(glycolic)acid, poly(lactic acid), poly(hydroxy acids), polydioxanone, polycaprolactone, poly(ortho esters), poly(anhydrides), polyphosphazenes, poly(amino acids), pseudo-poly(amino acids), conductive polymers (such as polyacetylene, polypyrrole, polyaniline), or polyurethane or their potential copolymers. In some instances, a composition here comprise ECM and both a natural and a synthetic polymer. A composition herein can be a multi-material by linking an ECM and another polymer material, for example, via reaction with amines, free thiols, or short peptides that can be self-assembled with the ECM.

In some instances, a polymer of the composition is biocompatible and biodegradable and/or bioabsorbable, and can be a random copolymer, block copolymer or blend of monomers, homopolymers, copolymers, and/or heteropolymers that contain these monomers. Exemplary biodegradable or bioabsorbable polymers include, but are not limited to: polylactides, poly-glycolides, polycarprolactone, polydioxane and their random and block copolymers. A biodegradable and/or bioabsorbable polymer can contain a monomer selected from the group consisting of a glycolide, lactide, dioxanone, caprolactone, trimethylene carbonate, ethylene glycol and lysine. The biodegradable and/or bioabsorbable polymers can contain bioabsorbable and biodegradable linear aliphatic polyesters such as polyglycolide (PGA) and its random copolymer poly(glycolide-co-lactide-) (PGA-co-PLA). Other examples of suitable biocompatible polymers are polyhydroxyalkyl methacrylates including ethylmethacrylate, and hydrogels such as polyvinylpyrrolidone and polyacrylamides. Other suitable bioabsorbable materials are biopolymers which include collagen, gelatin, alginic acid, chitin, chitosan, fibrin, hyaluronic acid, dextran, polyamino acids, polylysine and copolymers of these materials. Any combination, copolymer, polymer or blend thereof of the above examples is contemplated for use according to the present invention. Such bioabsorbable materials may be prepared by known methods.

Therefore, methods are described herein for preparing a composition comprising decellularized ECM derived from skeletal muscle tissue. The invention also provides ECM compositions and methods derived from skeletal muscle tissue in an analogous process. Related compositions, devices and methods of production and use also are provided. In some instances a composition comprises cross-linkers including, but not limited to, common collagen crosslinkers, hyaluronic acid crosslinkers, or other protein cross-linkers with altered degradation and mechanical properties. The compositions which may include cells or other therapeutic agents may be implanted into a patient, human or animal, by a number of methods. In some instances, the compositions are injected as a liquid into a desired site in the patient.

In certain embodiments, the viscosity of the composition increases when warmed above room temperature including physiological temperatures approaching about 37° C. According to one non-limiting embodiment, the ECM-derived composition is an injectable solution at room temperature and other temperatures below 35° C. In another non-limiting embodiment the gel can be injected body temperature above about 37° C. or near body temperature, but gels more rapidly at increasing temperatures. A gel forms after approximately 15-20 minutes at physiological temperature of 37° C. A general set of principles for preparing an ECM-derived gel is provided along with preferred specific protocols for preparing gels in the following Examples which are applicable and adaptable to numerous tissues including without limitation the skeletal muscle.

Commercially available ECM preparations can also be combined in the methods, devices and compositions described herein. In one embodiment, the ECM is derived from small intestinal submucosa (SIS). Commercially available preparations include, but are not limited to, SURGISIS™, SURGISIS-ES™, STRATASIS™, and STRATASIS-ES™ (Cook Urological Inc.; Indianapolis, Ind.) and GRAFTPATCH™ (Organogenesis Inc.; Canton, Mass.). In another embodiment, the ECM is derived from dermis. Commercially available preparations include, but are not limited to PELVICOL™ (sold as PERMACOL™ in Europe; Bard, Covington, Ga.), REPLIFORM™ (Microvasive; Boston, Mass.) and ALLODERM™ (LifeCell; Branchburg, N.J.).

In some instances, the solution, gel form, and adsorbed form of the skeletal muscle extracellular matrix of the invention provide all the constituents at the similar ratios found in vivo. For therapeutic treatment, the skeletal muscle extracellular matrix of the invention can be delivered which can allow for skeletal muscle or other relevant tissue repair or regeneration. For in vitro cell culture for skeletal muscle cells and other relevant cells, the gel and adsorbed forms of the skeletal muscle extracellular matrix of the invention contain all or many of the same extracellular matrix cues that the cells recognize in vivo as compared to the commonly used collagen, laminin, SURECOAT (CELLUTRON, mixture of collagen and laminin), and gelatin.

The compositions herein provide a particulate, powder, emulsion, gel or solution form of skeletal muscle extracellular matrix, and the use of these forms of skeletal muscle extracellular matrix for skeletal muscle or other relevant tissue repair or regeneration, for prevention or treatment of certain diseases. In one embodiment, the skeletal muscle tissue is first decellularized, leaving only the extracellular matrix. The matrix is then lyophilized, ground or pulverized into a fine powder, and solubilized with pepsin or other enzymes, such as, but not limited to, matrix metalloproteases, collagenases, and trypsin.

For gel therapy, the solution is then neutralized and brought up to the appropriate concentration using PBS/saline. In one embodiment, the solution can then be injected through a needle into the injured tissue or a tissue in need. The needle size can be without limitation 22 g, 23 g, 24 g, 25 g, 26 g, 27 g, 28 g, 29 g, 30 g, or smaller. In one embodiment, the needle size through which the solution is injected is 27 g. Delivery can also occur through a balloon infusion catheter or other non-needle catheter. Dosage amounts and frequency can routinely be determined based on the varying condition of the injured tissue and patient profile. At body temperature, the solution can then form into a gel. In yet another embodiment, gel can be crosslinked with glutaraldehye, formaldehyde, bis-NHS molecules, or other crosslinkers.

In yet another embodiment, the ECM can be combined with other therapeutic agents, such as cells, peptides, proteins, DNA, drugs, nutrients, antibiotics, survival promoting additives, proteoglycans, and/or glycosaminolycans. In yet another embodiment, the ECM can be combined and/or crosslinked with a synthetic polymer. Examples of synthetic polymers include, but are not limited to: polyethylene terephthalate fiber (DACRON™), polytetrafluoroethylene (PTFE), polylactic acid (PLA), polyglycolic acid (PGA), polyethylene glycol (PEG), poly(ethylene glycol) diacrylate (PEG diacrylate), polyethylene, polystyrene and nitinol.

In yet another embodiment, ECM solution or gel can be injected into the injured tissue or other relevant tissue in need, alone or in combination with above-described components for endogenous cell ingrowth, angiogenesis, and regeneration. In yet another embodiment, the ECM or ECM liquid can be sprayed on or into injured tissue or other relevant tissue in need, alone or in combination with above-described components for endogenous cell ingrowth, angiogenesis, and regeneration. In yet another embodiment, the composition can also be used alone or in combination with above-described components as a matrix to change mechanical properties of the skeletal muscle or other relevant tissues and/or to restore muscle mass and function. In yet another embodiment, the composition can be delivered with cells alone or in combination with the above-described components for regenerating muscle mass and function. In yet another embodiment, the composition can be used alone or in combination with above-described components for increasing arteriole and capillary density, as well as recruiting more desired cells for tissue repair and regeneration.

In one embodiment for making a soluble reagent, the solution is brought up in a low pH, neutral pH, or physiological pH solution including but not limited to 0.5 M, 0.1, or 0.01 M acetic acid or 0.1M HCl, PBS, or other buffering solutions to the desired concentration and then placed into tissue culture plates/wells, coverslips, scaffolding or other surfaces for tissue culture. After placing in an incubator at 37° C. for 1 hour, or overnight at room temperature, the excess solution is removed. After the surfaces are rinsed with PBS, cells can be cultured on the adsorbed matrix. The solution can be combined in advance with peptides, proteins, DNA, drugs, nutrients, survival promoting additives, proteoglycans, and/or glycosaminoglycans before, during, or after injection/implantation.

The present invention provides enhanced cell attachment and survival on both the therapeutic composition and adsorbed cell culturing composition forms of the skeletal muscle extracellular matrix in vitro. The soluble cell culturing reagent form of the skeletal muscle extracellular matrix induces faster spreading, faster maturation, and/or improved survival for skeletal muscle cells and other relevant cells compared to standard plate coatings.

In an embodiment herein, a biomimetic ECM derived from native skeletal muscle tissue is disclosed. In some instances, a matrix resembles the in vivo skeletal muscle or other relevant tissue environment in that it contains many or all of the native chemical cues found in natural skeletal muscle ECM. In some instances, through crosslinking or addition or other materials, the mechanical properties of healthy adult or embryonic skeletal muscle can also be mimicked. As described herein, skeletal muscle ECM can be isolated and processed into a gel using a simple and economical process, which is amenable to scale-up for clinical translation.

In some instances, a composition as provided herein can comprise a matrix and exogenously added or recruited cells. The cells can be any variety of cells. In some instances, the cells are a variety of skeletal muscle or relevant cells including, but not limited to: stem cells, progenitors, skeletal muscle precursor cells, and fibroblasts derived from autologous or allogeneic sources.

The invention thus provides a use of a gel made from native decellularized skeletal muscle extracellular matrix to support isolated neonatal skeletal muscle or stem cell progenitor derived skeletal muscle cells in vitro and to act as an in situ gelling scaffold, providing a natural matrix to improve cell retention and muscle mass restoration. A scaffold created from skeletal muscle ECM is well-suited for cell transplantation in the injured tissue, since it more closely approximates the in vivo environment compared to currently available materials.

A composition herein comprising skeletal muscle ECM and exogenously added cells can be prepared by culturing the cells in the ECM. In addition, where proteins such as growth factors are added into the extracellular matrix, the proteins may be added into the composition, or the protein molecules may be covalently or non-covalently linked to a molecule in the matrix. The covalent linking of protein to matrix molecules can be accomplished by standard covalent protein linking procedures known in the art. The protein may be covalently or linked to one or more matrix molecules.

In one embodiment, when delivering a composition that comprises the decellularized skeletal muscle ECM and exogenous cells, the cells can be from cell sources for treating certain diseases that include allogeneic, xenogeneic, or autogenic sources. Accordingly, embryonic stem cells, fetal or adult derived stem cells, induced pluripotent stem cells, skeletal muscle progenitors, fetal and neonatal skeletal muscle cells, mesenchymal cells, parenchymal cells, epithelial cells, endothelial cells, mesothelial cells, fibroblasts, hematopoietic stem cells, bone marrow-derived progenitor cells, skeletal cells, macrophages, adipocytes, and autotransplanted expanded skeletal cells can be delivered by a composition herein. In some instances, cells herein can be cultured ex vivo and in the culture dish environment differentiate either directly to skeletal muscle cells, or to bone marrow cells that can become skeletal muscle cells. The cultured cells are then transplanted into the mammal, either with the composition or in contact with the scaffold and other components.

Adult stem cells are yet another species of cell that can be part of a composition herein. Adult stem cells are thought to work by generating other stem cells (for example those appropriate to skeletal muscle) in a new site, or they differentiate directly to a skeletal muscle cells in vivo. They may also differentiate into other lineages after introduction to organs, such as the skeletal muscle. The adult mammal provides sources for adult stem cells in circulating endothelial precursor cells, bone marrow-derived cells, adipose tissue, or cells from a specific organ. It is known that mononuclear cells isolated from bone marrow aspirate differentiate into endothelial cells in vitro and are detected in newly formed blood vessels after intramuscular injection. Thus, use of cells from bone marrow aspirate can yield endothelial cells in vivo as a component of the composition. Other cells which can be employed with the invention are the mesenchymal stem cells administered with activating cytokines. Subpopulations of mesenchymal cells have been shown to differentiate toward skeletal muscle generating cell lines when exposed to cytokines in vitro.

Human embryonic stem cell derived skeletal muscle cells can be grown on a composition herein comprising the skeletal muscle ECM of the present invention. In some instances, hESC-derived skeletal muscle cells grown in the presence of a composition herein provide a more in vivo-like morphology. In some instances, hESC-derived skeletal muscle cells grown in the presence of a composition herein provide increased markers of maturation.

The invention is also directed to a drug delivery system comprising decellularized skeletal muscle extracellular matrix for delivering cells, drugs, molecules, or proteins into a subject for treating defective, diseased, damaged, ischemic, ulcer or other injured tissues or organs. In one embodiment, the inventive biocompatible skeletal muscle ECM material comprising the decellularized skeletal muscle extracellular matrix alone or in combination with other components is used for treating muscle degeneration, and other diseases to increase arteriole and capillary density and restore muscle mass and function. Therefore, the inventive biocompatible ECM material can be used to transplant cells, or injected alone to recruit native cells or other cytokines endogenous therapeutic agents, or act as a exogenous therapeutic agent delivery vehicle.

The composition of the invention can further comprise cells, drugs, proteins, or other biological material such as, but not limited to, erythropoietin (EPO), stem cell factor (SCF), vascular endothelial growth factor (VEGF), transforming growth factor (TGF), fibroblast growth factor (FGF), epidermal growth factor (EGF), cartilage growth factor (CGF), nerve growth factor (NGF), keratinocyte growth factor (KGF), skeletal growth factor (SGF), osteoblast-derived growth factor (BDGF), hepatocyte growth factor (HGF), insulin-like growth factor (IGF), cytokine growth factor (CGF), stem cell factor (SCF), platelet-derived growth factor (PDGF), endothelial cell growth supplement (EGGS), colony stimulating factor (CSF), growth differentiation factor (GDF), integrin modulating factor (IMF), calmodulin (CaM), thymidine kinase (TK), tumor necrosis factor (TNF), growth hormone (GH), bone morphogenic proteins (BMP), matrix metalloproteinase (MMP), tissue inhibitor matrix metalloproteinase (TIMP), interferon, interleukins, cytokines, integrin, collagen, elastin, fibrillins, fibronectin, laminin, glycosaminoglycans, hemonectin, thrombospondin, heparan sulfate, dermantan, chondroitin sulfate (CS), hyaluronic acid (HA), vitronectin, proteoglycans, transferrin, cytotactin, tenascin, and lymphokines.

Tissue culture plates can be coated with either a soluble ligand or gel form of the extracellular matrix of the invention, or an adsorbed form of the extracellular matrix of the invention, to culture skeletal muscle cells or other cell types relevant to skeletal muscle tissue or other relevant tissue repair. This can be used as a research reagent for growing these cells or as a clinical reagent for culturing the cells prior to implantation. The extracellular matrix reagent can be combined with other tissue matrices and cells.

For gel reagent compositions, the solution is then neutralized and brought up to the appropriate concentration using PBS/saline or other buffer, and then be placed into tissue culture plates and/or wells. Once placed in an incubator at 37° C., the solution forms a gel that can be used for any 2D or 3D culture substrate for cell culture. In one embodiment, the gel composition can be crosslinked with glutaraldehye, formaldehyde, bis-NHS molecules, or other crosslinkers, or be combined with cells, peptides, proteins, DNA, drugs, nutrients, survival promoting additives, proteoglycans, and/or glycosaminolycans, or combined and/or crosslinked with a synthetic polymer for further use.

The invention further provides an exemplary method of culturing cells adsorbed on a decellularized skeletal muscle extracellular matrix comprising the steps of: (a) providing a solution comprising the biocompatible material of decellularized skeletal muscle ECM in low pH solution or approximately neutral or physiological pH including but not limited to, 0.5 M, or 0.01 M acetic acid or 0.1M HCl or PBS or any other buffered solution to a desired concentration, (b) placing said solution into tissue culture plates or wells, (c) incubating said tissue culture plates or wells above room temperature such as at 37° C., for between 1 hour and overnight (or at room temperature to 40° C.), (d) removing excess solution, (e) rinsing said tissue culture plates or wells with PBS, and (f) culturing cells on the adsorbed matrix. Cells that can be cultured on the adsorbed matrix comprising the skeletal muscle extracellular matrix of the invention include skeletal muscle cells or other cell types relevant to skeletal muscle repair, including stem cells and skeletal muscle cell progenitors.

Skeletal myoblasts plated on skeletal muscle matrix displayed a significant increase in i) the number of myosin heavy chain positive myotubes, ii) the number of nuclei per myotube and iii) myotube width when compared to cells plated on traditional collagen type I coated substrates. In some instances, the compositions are configured to provide the ability to reconstitute the in vivo muscle ECM. The composition may provide a tool to assess and maintain muscle and stem cell behavior in vitro similar to the native state, and may provide a tool for cell-mediated therapies in vivo.

In one instance, a method of making the composition herein comprises electrospinning. In some instances, a method herein is configured to control the nanofiber size, shape, or thickness. In some instances, contractility can be induced into the composition, for example, with cells or external pacing. Contractility can create cyclic stress to promote a more natural skeletal muscle. In some instances, cell influx and angiogenesis can be induced into the composition, for example, when the composition comprises linked groups or embedded factors, such as angiogenic factors.

In some instances, a composition herein may contain microbeads. Microbeads can be a part of the composition or delivered by the composition. Exemplary microbeads can be any variety of materials, for example, natural or synthetic. In some instances, the microbeads can have varied degradation properties or comprise, for example, MMP inhibitors, growth factors, or small molecules.

In some instances, the composition can comprise a biological group that can act as an adhesive or anchor where the composition is delivered. In one instance, a composition can be a bioadhesive, for example, for wound repair. In some instances, a composition herein can be configured as a cell adherent. For example, the composition herein can be coating or mixed with on a medical device or a biologic that does or does not comprises cells. For example, the composition herein can be a coating for a synthetic polymer graft. In some instances, the composition includes an anti-bacterial or anti-bacterial agents could be included. Methods herein can comprise delivering the composition as a wound repair device. In one instance, a composition comprises an alginate bead that is coated with an ECM composition as described herein.

In some instances, the composition is injectable. An injectable composition can be, without limitation, a powder, liquid, particles, fragments, gel, or emulsion. The injectable composition can be injected into an injured tissue or organ. The compositions herein can recruit, for example without limitation, endothelial, smooth muscle, skeletal muscle, progenitors, and stem cells.

The composition of the present invention can be developed for substrate coating for a variety of applications. In some instances, the ECM of the composition retains a complex mixture of muscle-specific ECM components after solubilization. In some instances, the coatings herein can more appropriately emulate the native muscle ECM in vitro.

In some instances, a composition herein is a coating. The coating can comprise an ECM from any tissue for example cardiac muscle, skeletal muscle, pericardium, liver, adipose tissue, and brain. A coating can be used for tissue culture applications, both research and clinical. The coating can be used to coat, for example without limitation, synthetic or other biologic scaffolds/materials, or implants. In some instances, a coating is texturized or patterned. In some instances, a method of making a coating includes adsorption or chemical linking. A thin gel or adsorbed coating can be formed using an ECM solution form of the composition. In some instances, a composition herein is configured to seal holes in the heart such as septal defects. The compositions of the present invention may be used as coating for biologics, medical devices or drug delivery devices.

The native ECM is a complex combination of fibrous proteins and proteoglycans that can affect many aspects of cellular behavior. To regenerate tissue, a scaffold should mimic this native microenvironment. The present invention, therefore, provides an injectable hydrogel derived from skeletal muscle ECM, which mimics the native biochemical cues, as well as being amenable to minimally invasive, injectable procedures, providing an advantage for treating muscle degeneration. In certain embodiments, the invention can be used as a delivery vehicle combined with cells and/or growth factors. In certain embodiments of the invention, the compositions and methods herein provide skeletal muscle ECM material as an acellular stand-alone therapy, which is used to recruit endogenous cells for neovascularization and repair. In certain embodiments, the present invention provides a porcine source of skeletal muscle matrix. Xenogeneic decellularized extracellular matrices are biocompatible upon removal of the cellular antigens, and can be utilized in the clinic for a number of surgical repair applications.

A liquid version of skeletal muscle matrix herein can form a porous scaffold upon injection, which promotes cellular infiltration to the damaged area. In certain embodiments, remnant growth factors are present. In other embodiments, remnant growth factors are not present. In methods herein, the decellularization and subsequent processing into the hydrogel form decreases the probability of the presence of remnant growth factors.

In the present invention, mitogenic properties of the degradation products of the skeletal muscle ECM material were assessed on smooth muscle cells, a relevant cell type for vascularization. The skeletal muscle matrix degradation fragments induced a higher proliferation rate compared to collagen. Extracellular matrix degradation products sometimes have mitogenic activity. The examples herein provide evidence that the injectable skeletal muscle matrix scaffold induces neovascularization in vivo.

Therefore, the ability of this present scaffold to induce neovascularization was then assessed in a rat hindlimb ischemia model compared to collagen, which is the predominant component of the skeletal muscle matrix and a commonly utilized scaffold. Not only was the vessel density higher in the skeletal muscle matrix, but there were significantly more large-diameter vessels greater than 25 µm, indicating maturation of the vasculature. Additionally, significance was seen as early as three days post-injection demonstrating the fast rate of vascularization. The presence of more mature vasculature indicates permanence of the formed vessels, which is important to getting a vascular supply as quickly as possible to the ischemic region, and to maintain blood flow (Banker and Goslin, 1998).

In certain embodiments, the liquid form of decellularized skeletal muscle, when utilized as a coating for cell culture, increased skeletal myoblast differentiation compared to collagen coatings. In certain embodiments, the composition provides tissue specific biochemical cues to recapitulate the skeletal muscle microenvironment. The invention demonstrated that the degradation products of this scaffold increased myoblast proliferation compared to collagen, which is consistent with literature demonstrating the inhibitory effect of collagen on smooth muscle cells and fibroblasts (Koyama et al., 1996; Rhudy and McPherson, 1988).

Next, the infiltration of muscle cells into the scaffold in the hindlimb ischemia model was assessed. The number of desmin- and MyoD-positive cells that were recruited into the skeletal muscle matrix scaffold was measured as compared to that into the collagen. Desmin, a muscle specific protein, confirms that the cells that infiltrated were from a myogenic origin. MyoD, on the other hand, is a specific striated muscle regulatory transcription factor, which coordinates the myogenic program in differentiating myoblasts (Kanisicak et al., 2009; Lee et al., 2000; Wada et al., 2002). The invention provides that there were a significantly higher number of muscle cell types in the skeletal muscle matrix, and that many of these cells were also proliferating. The MyoD-positive cells also indicate that immature progenitor cell types are recruited to the skeletal muscle matrix. The presence of these MyoD-positive and desmin-positive muscle cells indicate that the skeletal muscle scaffold is recruiting relevant cell types that aid in the regeneration of the damaged muscle, in addition to treating the ischemic tissue.

The present invention, thus, provides an acellular, biomaterial-only therapy for treating muscle degeneration. Previous biomaterial strategies have only utilized scaffolds to enhance cell or growth factor therapy (Doi et al., 2007; Jay et al., 2008; Kong et al., 2008; Layman et al., 2007; Lee et al., 2010; Ruvinov et al., 2010; Silva and Mooney, 2007). To increase its therapeutic benefit, the invention can be used in conjunction with cell or growth factor therapy as these components can be added to the biomaterial prior to injection. To create a material that could be easily prepared in the clinic, a method that allowed for long-term storage of the injectable skeletal muscle matrix scaffold was also developed with only sterile water required to resuspend it immediately prior to use.

The invention is further illustrated by the following examples, which are not to be construed in any way as imposing limitations upon the scope thereof. It is apparent for skilled artisans that various modifications and changes are possible and are contemplated within the scope of the current invention.

EXAMPLES

Example 1

Injectable Skeletal Muscle Matrix

Figure 1B:
Figure 1C:
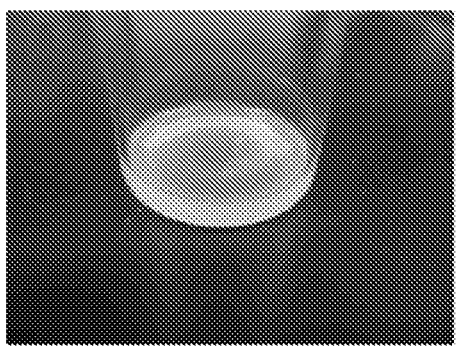
Figure 1D:
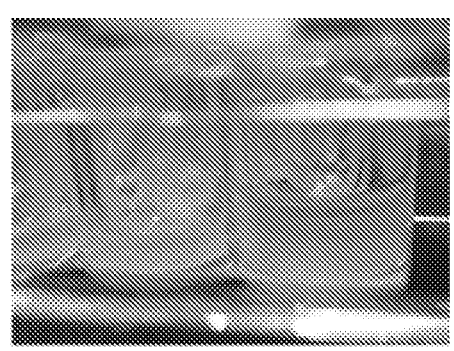
Figure 1E:
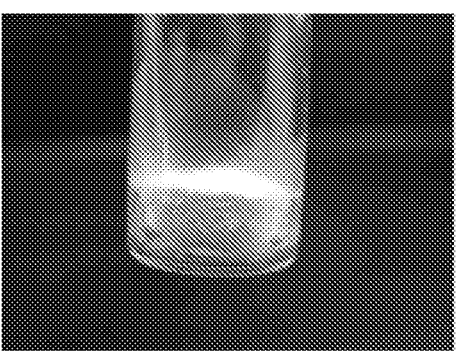
Figure 1F:

Skeletal muscle matrix material was derived through decellularization of porcine skeletal muscle tissue (FIG. 1A). Fat and connective tissue was removed, and the skeletal muscle was cut into ~1 cm3 pieces, rinsed with deioninized water and stirred in 1% (wt/vol) solution of SDS in PBS for 4-5 days. The decellularized muscle was then stirred overnight in deionized water, and agitated rinses under running deionized water were performed to remove residual SDS. In addition to confirmation with lack of nuclei on H&E stained sections (not shown), the DNA content of the material was measured as 26.14±1.67 ng of DNA/mg of dry weight ECM, which confirmed decellularization. The matrix was then lyophilized (FIG. 1B) and milled into a fine particulate. At this stage the material can be hydrated and utilized for in vivo injection or it can be enzymatically digested to form a liquid (FIG. 1C). At this stage, the liquid skeletal muscle matrix can be diluted and utilized as a coating for cell culture, or can be brought to physiological pH and temperature, which triggers assembly into a hydrogel (FIG. 1D). After raising the pH of the material to 7.4 at room temperature, the material can also be re-lyophilized (FIG. 1E) for long-term storage at −80° C. The material can then be resuspended at a later date using only sterile water (FIG. 1F) and utilized for in vivo injection.

Example 2

Mitogenic Assay

Figure 2A:
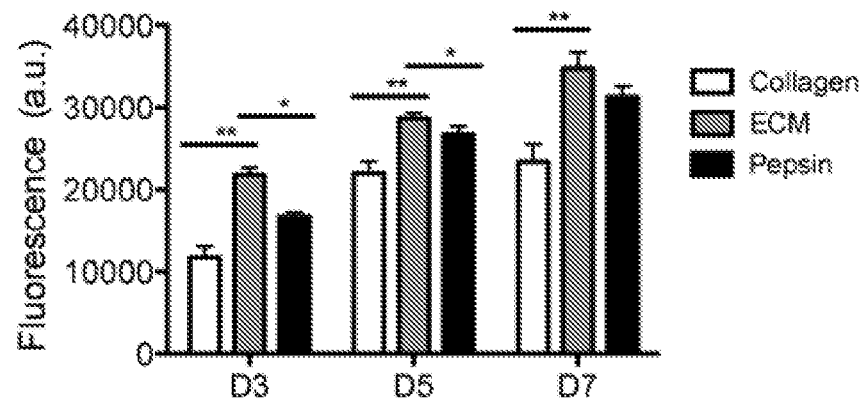
FIGS. 2A-2B illustrate in vitro mitogenic activity assay.
Figure 2B:
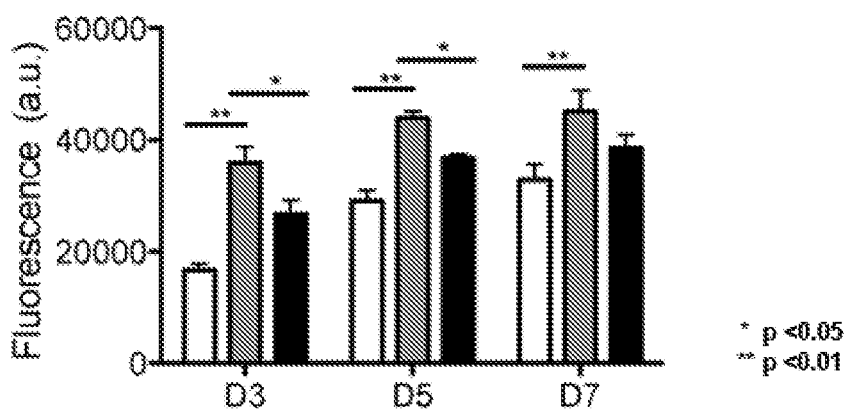

Degradation products of decellularized ECMs have been previously shown to have mitogenic activity. It was examined whether the degradation products of the skeletal muscle matrix hydrogel had a mitogenic effect on cells in vitro. Proliferation of smooth muscle cells and skeletal myoblasts following exposure to either enzymatically degraded skeletal muscle ECM or collagen was assessed. Pepsin was also included as a control, as pepsin was utilized to digest the matrix material. A Picogreen assay was used to determine double stranded DNA content at days 3, 5, and 7 in culture to quantify cell proliferation. It was found that both smooth muscle cells (FIG. 2A) and myoblasts (FIG. 2B), when cultured in media containing degraded skeletal muscle matrix, had a higher rate of proliferation compared to cells cultured in media containing the same concentration of collagen. The increase in cell number was significantly greater at all time points ($p<0.01$). At day 3, there was a 1.85-fold increase in cell number in the skeletal muscle matrix wells compared to collagen for the smooth muscle cells, and a corresponding 2.15-fold increase with the skeletal myoblasts. There was also a 1.3 fold increase for skeletal muscle matrix wells compared to pepsin for both cell types, while the pepsin and collagen controls were not statistically different. Thus, degradation products of the skeletal muscle matrix were shown to promote mitogenic activity in both cell types in vitro when compared to collagen or the pepsin control.

Example 3

Gelation In Vitro and In Vivo

Figure 3:
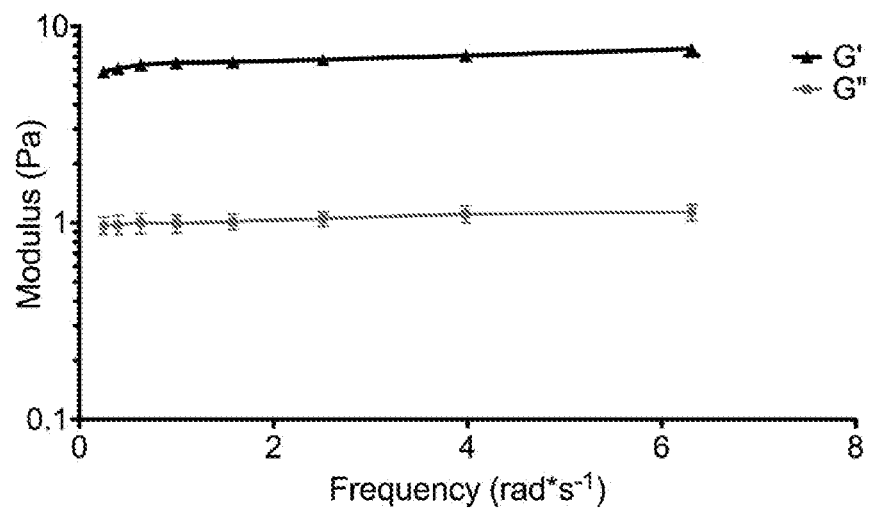
FIG. 3 illustrates Rheological data. A representative trace of the storage (G') and loss (G") moduli for the skeletal muscle matrix gel is shown.
Figure 4A:
FIGS. 4A-4C illustrate skeletal muscle matrix delivery and gelation in situ.
Figure 4B:
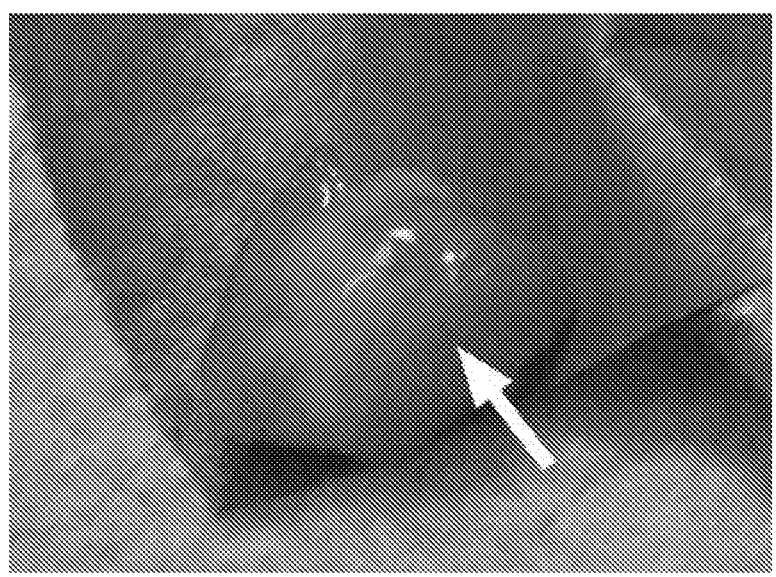
Figure 4C:
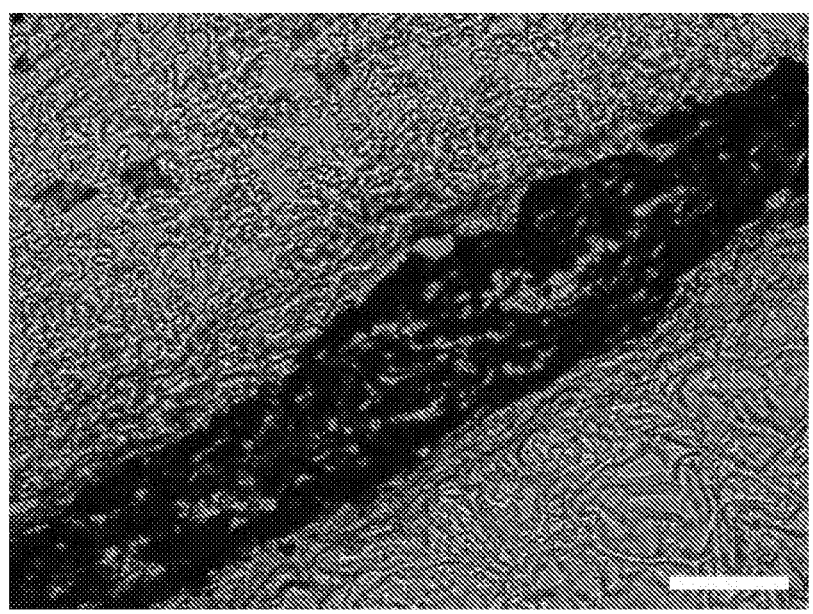
Figure 5A:
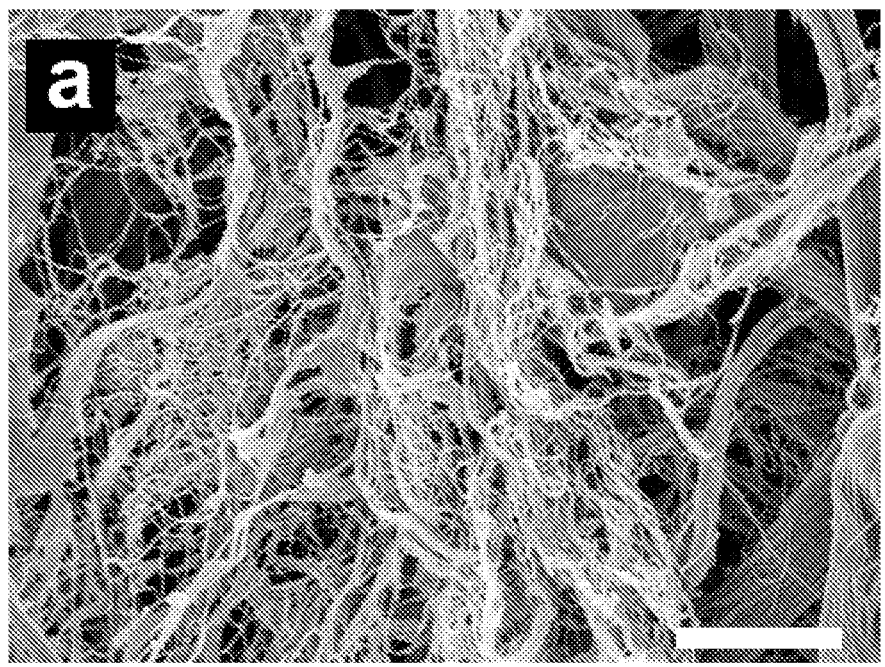
FIGS. 5A-5B illustrate scanning electron microscopy. Micrograph of a cross-section of skeletal muscle matrix formed FIG. 5A in vitro, and FIG. 5B 20 minutes post-subcutaneous injection. Note the formation of the assembled fibers on the nano- and micro-scale. Scale bar at 100 µm.
Figure 5B:
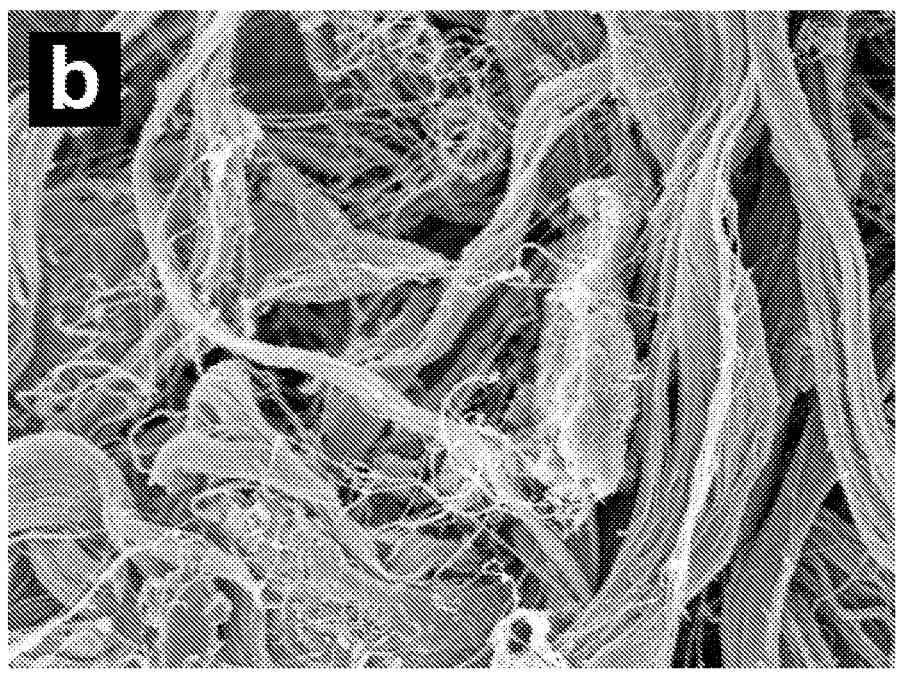
Figure 10A:
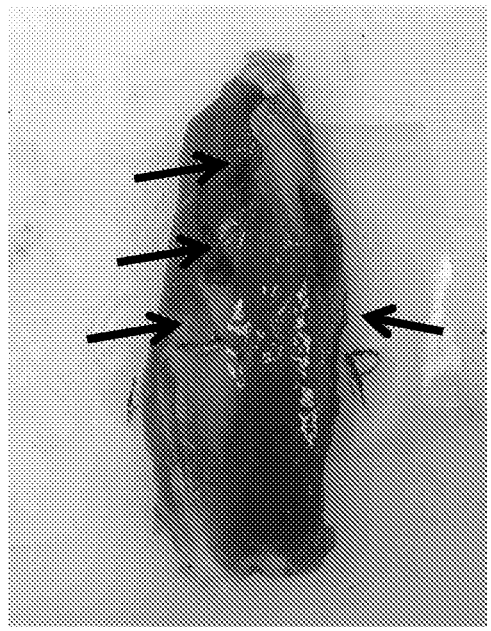
FIGS. 10A-10B illustrate skeletal muscle matrix delivery and gelation in situ.
Figure 10B:
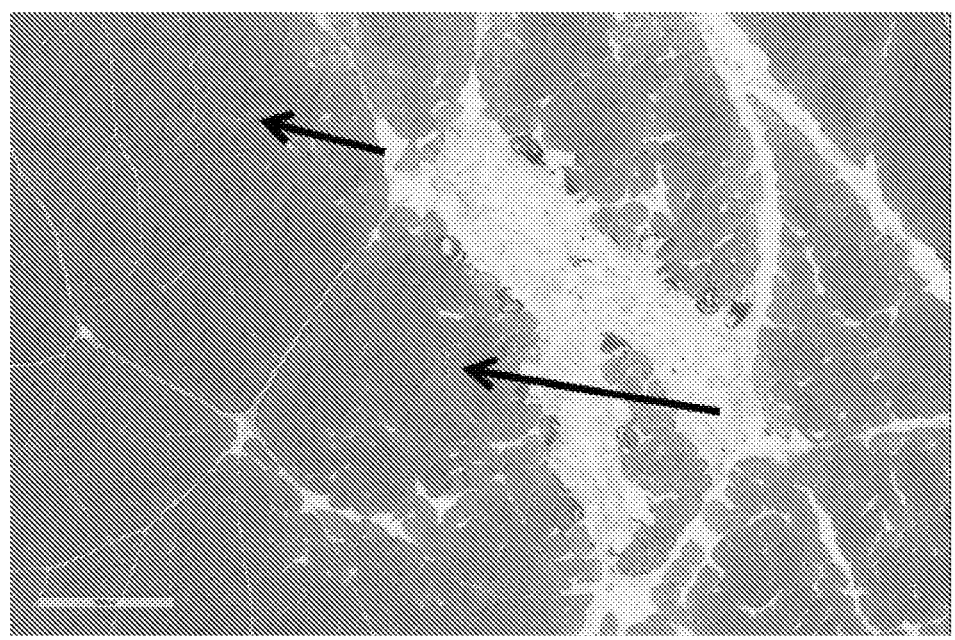

A gel form of the matrix was initially made in vitro by bringing the material (6 mg/mL) to a physiological pH and incubating the material at 37° C. After gelation, the material was tested for rheological properties where it was determined that the material had a storage modulus (G') of 6.5±0.5 Pa. A representative trace of rheological data is shown in FIG. 3. The ability of the liquid skeletal muscle matrix to form a gel in situ were then assessed by injecting the material into a healthy rat hindlimb. For all in vivo studies, liquid skeletal muscle matrix, which had been biotinylated and re-lyophilized for storage at −80 C were utilized. Prior to injection, the material was resuspended in sterile water alone. The skeletal muscle matrix was then loaded into a syringe and injected intramuscularly into a rat hindlimb (FIG. 4A). To determine whether the skeletal muscle matrix would assemble and form a scaffold, the injection region was excised after 20 minutes. A visible gel, denoted by the white region in FIG. 4B, was observed within the muscle. Additional matrix injections were cryosectioned and stained to visualize the biotinylated matrix. The liquid skeletal muscle matrix assembled into a fibrous scaffold once in vivo (FIG. 4C). In addition, the skeletal muscle matrix was also demonstrated to form a hydrogel upon in situ injection directly into rabbit supraspinatus muscle (FIGS. 10A and 10B). To assess the microarchitecture of the skeletal muscle matrix hydrogel, the material was injected subcutaneously, and excised after 20 minutes. Scanning Electron Microscopy (SEM) demonstrated that the matrix forms a porous, fibrous scaffold, both in vitro and in vivo, that is composed of fibers on the nano- and micro-scale (FIG. 5).

Example 4

Cellular Infiltration and Neovascularization

Upon confirmation that the material was able to assemble upon injection, the skeletal muscle matrix hydrogel were then examined in a rat hindlimb ischemia model to assess its potential. One week post-hindlimb ischemia, either skeletal muscle matrix or collagen was injected intramuscularly below the site of femoral artery resection. At 3, 5, 7 or 14 days post-injection, the muscle was harvested to determine cellular infiltration. The hydrogel was still present at all time points, although it had significantly degraded by day 14. At each time point, the amount of neovascularization, which would be critical to treat the ischemic tissue, as well as the number of muscle cells and muscle progenitors, which could aid in repair of the damaged tissue, were assessed.

Figure 7A:
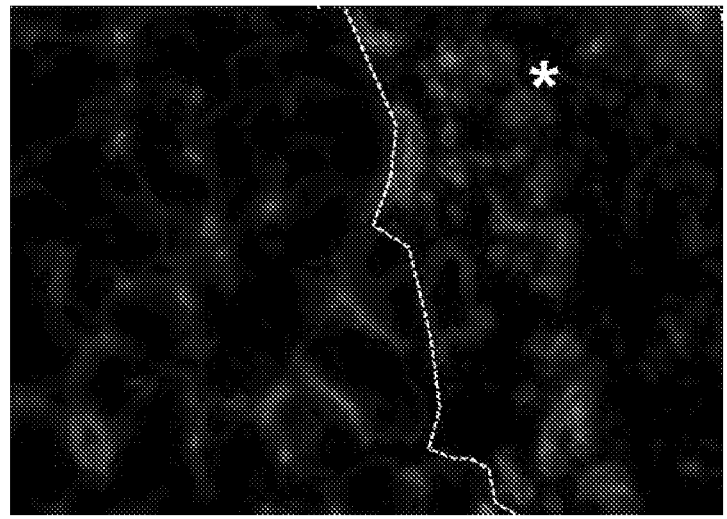
FIGS. 7A-7C illustrates quantification of endothelial cell recruitment.
Figure 7B:
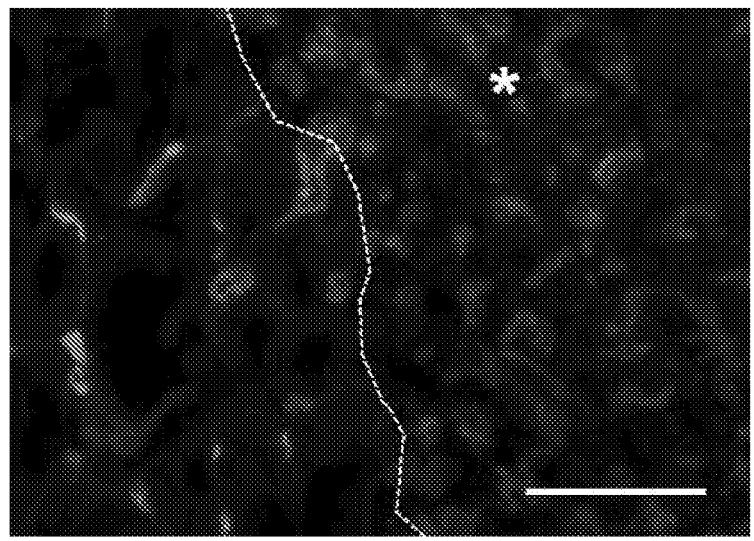
Figure 7C:
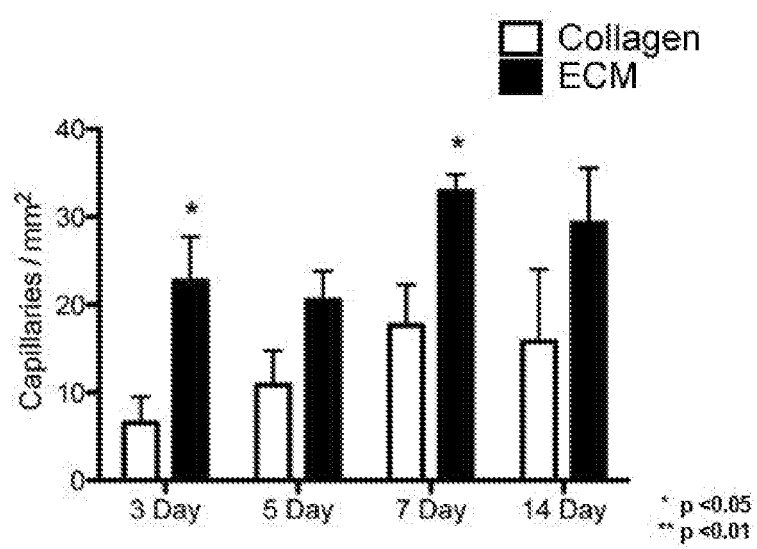

To determine whether the acellular scaffold would support new vessel formation in vivo, smooth muscle cells in collagen (FIG. 6A) and skeletal muscle matrix (FIG. 6B) injected regions were labeled via immunohistochemistry. Arteriole density was significantly greater in the skeletal muscle matrix injection region compared to collagen at 3, 5, and 7 days post-injection (FIG. 6C), with many of the vessels having an average diameter greater than 25 μm (FIG. 6D). While not significant, there was still a distinct trend towards an increase in vasculature at day 14 following injection of the skeletal muscle matrix hydrogel. Additionally, endothelial cell infiltration was measured in collagen (FIG. 7A), and skeletal muscle matrix (FIG. 7B) injection regions. Endothelial cell density was found to be similar across all four time points, but was significantly greater in the skeletal muscle matrix injection region at 3 and 7 days post-injection (FIG. 7C).

Figure 8A:
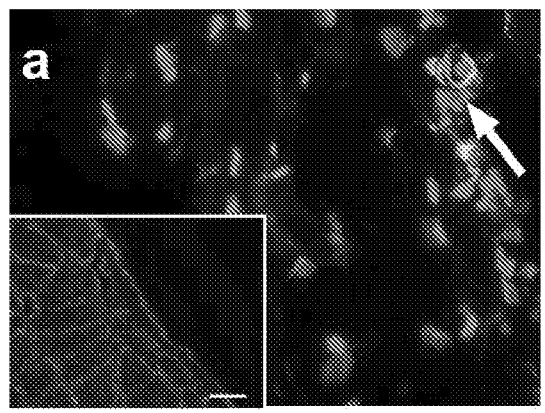
FIGS. 8A-8D illustrates proliferating muscle cell recruitment.
Figure 8B:
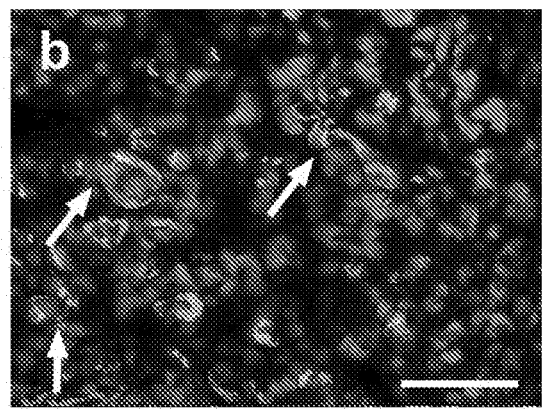
Figure 8C:
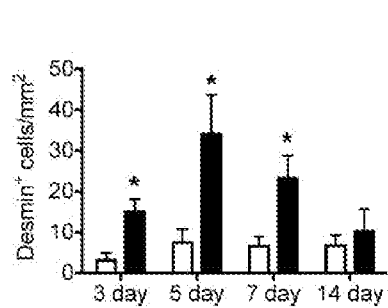
Figure 8D:
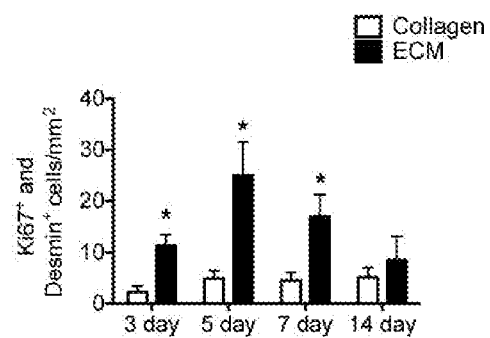

It was then determined whether muscle cells were also recruited to the injection site using staining against desmin (FIG. 8A, 8B). The desmin positive cells were also co-stained for Ki67, a marker for proliferation, as denoted by the arrows in FIGS. 8A, 8B. The skeletal muscle matrix recruited significantly more desmin-positive cells when compared to the collagen matrix at 3, 5, and 7 days post-injection, a the trend that continued at day 14 (FIG. 8C). Moreover, the majority of cells expressing desmin also were Ki67 positive, indicating proliferating muscle cells were infiltrating the injection region (FIG. 8D). The number of Ki67 and desmin positive cells was significantly increased at 3, 5, and 7 days post-injection, with the same trend at day 14.

Figure 9A:
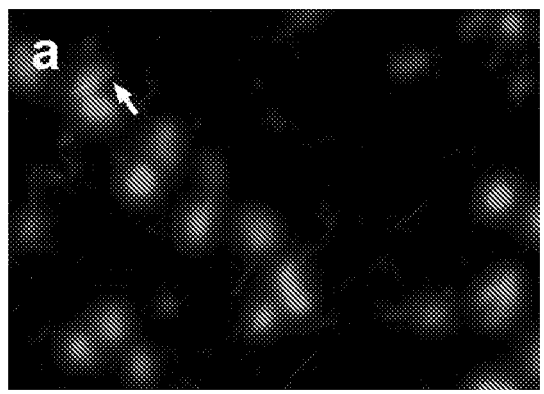
FIGS. 9A-9C illustrate muscle progenitor infiltration. MyoD positive cells (green greyscale) in FIG. 9A collagen and FIG. 9B skeletal muscle matrix injection regions at 5 days. Area of injection is denoted by the dotted line. Scale bar at 20 µm.
Figure 9B:
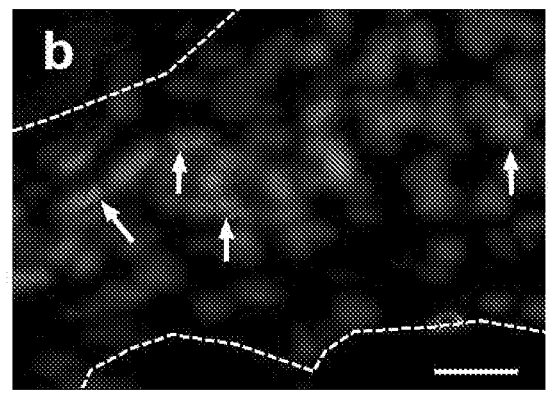
Figure 9C:
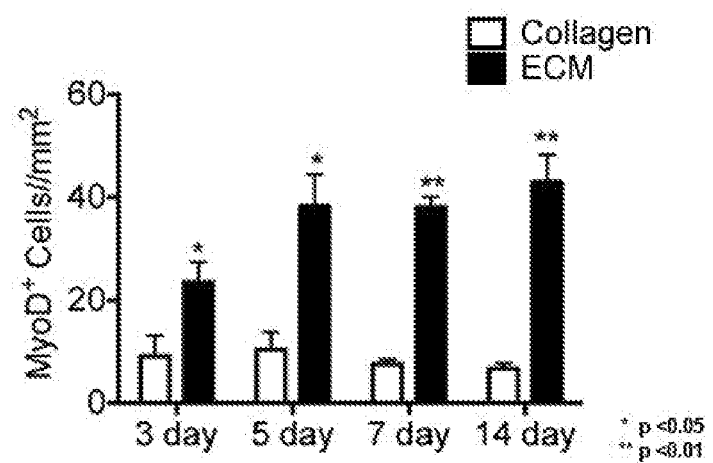

Cell infiltration was further assessed using MyoD as a marker for the potential recruitment of activated satellite cells. There was a low number of MyoD positive cells recruited into the injection region of both materials at the examined time points; however, there was a statistically significant increase in MyoD positive cells in the skeletal muscle matrix (FIG. 9). The MyoD staining was prevalently perinuclear, which has been shown in other studies.

Example 5

Injectable Skeletal Muscle Matrix Powder

After milling, the skeletal muscle matrix powder is hydrated with sterile water, saline, or PBS and injected or implanted into the injured limb. Depending on the concentration, the injected skeletal muscle matrix can form a bolus or spread throughout the tissue. Upon implantation, the skeletal muscle ECM particulate forms a scaffold and creates degradation products that recruit endogenous cells to repair the ischemic region. These cells include blood vessels, skeletal muscle cells, and skeletal muscle progenitors. By recruiting endogenous cells for repair and regeneration, the skeletal muscle matrix particulate has to potential to treat peripheral artery disease and critical limb ischemia, and the various complications associated with these diseases.

Example 6

Decellularization of Skeletal Muscle for Matrix Preparation

Skeletal muscle from the hindleg was harvested from Yorkshire pigs, approximately 30-45 kg, immediately after sedation with a ketamine/xylazine combination (25 mg/kg, 2 mg/kg respectively) and euthanasia with beuthanasia (1 mL/5 kg). Fat and connective tissue was removed, and the skeletal muscle was cut into ~1 $cm^3$ pieces and decellularized. Briefly, the tissue was rinsed with deionized water and stirred in 1% (wt/vol) solution of sodium dodecyl sulfate (SDS) in phosphate buffered saline (PBS) for 4-5 days. Decellularized skeletal muscle was stirred overnight in deionized water and then agitated rinses under running DI water were performed to remove residual SDS. A sample of decellularized matrix was frozen in Tissue Tek O.C.T. freezing medium, sectioned into 10 μm slices, and stained with hematoxylin and eosin (H&E) to confirm the absence of nuclei. Following the decellularization protocol, the ECM was lyophilized overnight and milled to a fine powder using a Wiley Mini Mill. Additionally, to quantify DNA content, the DNeasy assay (Qiagen, Valencia, Calif.) was performed according to manufacturer's instructions. After extraction, the Take3 plate was used to measure the concentration of DNA using a Synergy 2 microplate reader (Biotek, Winooski, Vt.).

Preparation of Injectable Skeletal Muscle Matrix and Collagen

In order to render the decellularized extracellular matrix (ECM) into a liquid form, the milled form of the matrix was subjected to enzymatic digestion. Pepsin (SIGMA, St. Louis, Mo.) was dissolved in 0.1 M hydrochloric acid (HCl) to make a 1 mg/ml pepsin solution and then filtered through a 0.22 μm filter (Millipore, Billerca, Mass.). The ECM at a ratio of 10:1 was digested in the pepsin solution under constant stirring. After approximately 48 hours, the matrix was brought to a physiological pH in a BSL-2 safety cabinet, and then either diluted for in vitro assays or for injection. For in vitro and in vivo studies, the skeletal muscle matrix was brought to a pH of 7.4 through the addition of sterile-filtered sodium hydroxide (NaOH) and 10×PBS, and further diluted to 6 mg/ml using 1×PBS inside a BSL-2 safety cabinet.

Skeletal Muscle Matrix In Vitro Gel Characterization

Gels of the skeletal muscle matrix were formed, at a concentration 6 mg/ml for rheological characteristics and for scanning electron microscopy. Either 100 μl of matrix was pipetted into a 96 well plate (Corning, Corning, N.Y.) or 500 μl in glass scintillation vials and incubated overnight to form gels. Rheometry was conducted on the 500 μl in vitro-formed skeletal muscle matrix gels using a TA instruments AR-G2 rheometer. The gels were tested using a 20 mm parallel plate geometry with a 1.2 mm gap at 37° C. Three frequency sweeps were performed within the linear viscoelastic strain region. Samples were run in triplicate and then the values were averaged to calculate the storage modulus.

Scanning electron microscopy (SEM) was utilized to determine the microstructure of the skeletal muscle matrix gels. These gels were either formed in vivo by injecting the skeletal muscle matrix subcutaneously in a rat and excised after 20 minutes, or in vitro after incubation of the material in a 96 well plate at 37° C. overnight. The skeletal muscle matrix gels were harvested and fixed with 2.5% glutaraldehyde for 2 hours, and then dehydrated using a series of ethanol rinses (30-100%). Samples were then critical point dried and coated with iridium using an Emitech K575X Sputter coater. Electron microscopy images were taken using a Phillips XL30 Environmental SEM Field Emission microscope at 10 kV, with 242 μA and a working distance of 10 mm In Vitro Proliferation Assays Primary rat aortic smooth muscle cells (RASMC) and C2C12 skeletal myoblasts were maintained on collagen coated plates and split at 1:5 every 2-3 days. Cells between passages 4 and 10 were plated at 750 cells/well in 96 well plates in growth media consisting of DMEM, 10% fetal bovine serum, and 1% pen-strep solution. Twenty-four hours later, the cells were washed with PBS to remove non-adherent cells. Digested skeletal muscle matrix and collagen were brought to a pH of 7.4, and then added to the growth media at concentrations of 0.05 mg/mL. As the ECM was enzymatically digested, pepsin was also included as a control at 0.005 mg/mL. All conditions were run in quadruplicate. Every two days, media was changed and cell proliferation was assessed using the PICOGREEN® assay (Invitrogen) per manufacturer's directions. Briefly, wells were rinsed in PBS and then incubated with 100 μL of TE buffer. After incubation for 30 minutes at room temperature followed by 5 minutes on a shaker, 100 μL of 1:200 Picogreen reagent was added. Upon covering the plates in foil and shaking them for 30 minutes, double stranded DNA was quantified using a fluorescent plate reader at 630 nm at days 3, 5, and 7.

In Vivo Gelation Test

To prepare for in vivo studies, a preliminary test was performed to ensure that the skeletal muscle matrix would be able to gel upon injection. The skeletal muscle matrix was labeled with biotin, and then injected into the hindlimbs of healthy Sprague Dawley rats. For biotin labeling, a 10 mM solution of EZ link Sulfo-NHS-Biotin (Pierce, Rockford, Ill.) was prepared and mixed with the liquid skeletal muscle matrix for a final concentration of 0.3 mg of biotin/mg matrix. The mixture was allowed to sit on ice for two hours. The skeletal muscle matrix was then frozen, lyophilized and stored at −80° C. until use. To resuspend the skeletal muscle matrix, sterile water was added at the original volume to bring the material to 6 mg/ml and vortexed. Female Harlan Sprague Dawley rats (225-250 g) were anesthetized using isoflurane at 5%, intubated, and maintained at 2.5% isoflurane during surgery. In preliminary studies, (n=2) 150 µl of skeletal muscle matrix was injected intramuscularly into healthy rats. The muscle was excised after 20 min, and fresh frozen using Tissue Tek O.C.T.

Hindlimb Ischemia Model

After confirmation of gelation in vivo, a rat hindlimb ischemia model was utilized to test the skeletal muscle extracellular matrix. Animals were placed in a supine position and hindlimb ischemia was induced by ligation and excision of the femoral artery. After ligation of the proximal end of the femoral artery, the distal portion of the saphenous artery was ligated and the artery and side branches were dissected free, and then excised. The area was sutured closed and animals were given an analgesic of 0.05 mg/kg of buprenorphine hydrochloride (Reckitt Benckiser Healthcare (UK) Ltd., Hull, England) prior to recovery from anesthesia. One week post-injury, the rats were anesthetized using 5% isoflurane, intubated, and maintained at 2.5% isoflurane for injection. Skeletal muscle matrix and rat tail collagen were biotinylated in order to visualize the injection region and 150 µl was injected intramuscularly. Injection was confirmed by a lightening of the muscle at the site of injection. Rats were sacrificed using an overdose of sodium pentobarbital (200 mg/kg) at 3, 5, 7, or 14 days post injection (n=4, except n=3 for 14 day collagen injection), and leg muscles were harvested and frozen in Tissue Tek O.C.T.

Histology and Immunohistochemistry

The excised muscle was cryosectioned into 10 µm slices. Slices were stained with Hematoxylin and Eosin every 1 mm and screened to determine the location of injected material. Adjacent slides were stained for visualization of biotin-labeled skeletal muscle matrix or collagen, to confirm the injection site. Slides were fixed in acetone, incubated with superblock buffer (Pierce), followed by 3% hydrogen peroxide (Sigma), and horseradish peroxidase conjugated neutravidin (Pierce) at room temperature. The reaction was visualized by incubation with diaminobenzidine (DAB, Pierce) for ten minutes.

Five slides evenly spaced within the injection region were then used for immunohistochemistry (IHC). Sections were fixed for 2 min in acetone and blocked with staining buffer for 1 h (2% goat serum and 0.3% Triton X-100 in PBS). Skeletal muscle sections were then assessed for vessel formation using a mouse anti-smooth muscle actin antibody (Dako, Carpinteria, Calif.; 1:75 dilution) to label smooth muscle cells. After three 5-minute washes with PBS, AlexaFluor 568 anti-mouse (Invitrogen, 1:200 dilution) was used as a secondary. Endothelial cell infiltration was assessed using FITC labeled isolectin (Vector Laboratories, Burlingame, Calif.; 1:100 dilution). Slides were then mounted using Fluoromount (Sigma). Sections stained with only the primary antibody or secondary antibody were used as negative controls. Images were taken at 100× using Carl Zeiss Observer D.1 and analyzed using AxioVision software. Arterioles were quantified with a visible lumen and a diameter ≥10 µm and normalized over the injection area.

In order to assess proliferating muscle cell infiltration into the injection region, sections were stained using a mouse anti-desmin antibody (Sigma; dilution 1:100) and co-stained with a rabbit anti-Ki67 (Santa Cruz Biotech, Santa Cruz, Calif.; dilution 1:100). AlexaFluor 488 anti-mouse and AlexaFluor 568 anti-rabbit were used for secondary antibodies (1:200), followed by staining with Hoechst 33342. Slides were mounted with Fluoromount (Sigma) prior to imaging. Additionally, the skeletal muscle tissue was assessed using a rabbit anti-MyoD (Santa Cruz Biotech, Santa Cruz, Calif.; dilution 1:100), followed by AlexaFluor 488 anti-rabbit as a secondary antibody, and Hoechst 33342. Three 400× images were taken per slide and analyzed using AxioVision software. The number of desmin positive cells, and desmin positive cells that co-localized with Ki67 were counted, averaged and normalized over the area. For the tissue sections analyzed for MyoD, the number of positive cells with MyoD co-localized with nuclei were counted and averaged over the area of injection.

Statistical Analysis

All data is presented as the mean±standard error of mean. For the in vitro assays, samples were run in quadruplicate and results were averaged. Significance was determined using a one-way analysis of variance (ANOVA) with a Bonferroni post-test. A two-tailed Student's t-test was used for all other data and reported as $p<0.05$ and $p<0.001$.

Example 7

Pelvic floor disorders (PFD) include urinary and fecal incontinence, and pelvic organ prolapse. Dysfunction of pelvic striated muscles, which include external urethral (EUS) and external anal (EAS) sphincteric muscles, and pelvic floor muscles (PFM) is a key factor in the pathogenesis of PFD. EAS and PFM dysfunction also implicated in the pathogenesis of Rectal Prolapse (RP). Furthermore, prevalence of PFD is substantially higher on female patients with RP compared to age-matched general female population. PFM dysfunction is thought to be a common etiological factor in the pathogenesis of these conditions.

I. Indication: Stress Urinary Incontinence (SUI) and Mixed Urinary Incontinence (MUI).

Patient population: Patients with SUI/MUI; Patients with SUI/MUI and intrinsic sphincter deficiency; Patients with SUI/MUI and pelvic floor muscle (PFM) dysfunction; Vaginally parous women.

Time-frames: 1. at the time of primary diagnosis of bothersome SUI/MUI; 2. as an adjunct therapy at the time of urethral bulking injection, sling procedure; 3. after failure to respond to other treatments for SUI (e.g. pelvic rehabilitation, urethral bulking injection, sling procedure); 4. at the time of diagnosis of recurrent bothersome SUI; 5. at the time of vaginal delivery.

Delivery Method: a) Delivery into urethral striated sphincter; Transurethral endoscopic approach: 0, 12, or 30-degree lens can be used; Approximately 4 ml volume of material is injected containing 2-50×10⁶ MDSCs. (Smaldone et al. MINERVA UROL NEFROL 2009) the myoblasts were suspended in 1.4 mL of Dulbecco's modified Eagle medium (DMEM)/F12 with 20% autologous serum, and the fibroblasts in 1 mL DMEM/F12 with 20% autologous serum mixed with 2.5 mL of collagen (Contigen®, Bard, Covington, Ga., USA) as carrier material to prevent them from migrating from the site of injection, as fibroblasts are mobile after application. Using a specially designed injection device, 15-18 aliquots (50-100 µL per depot) of the myoblast suspension were injected directly into the omega-shaped rhabdosphincter at two different levels, to promote regeneration of the muscle. Then 25-30 depots (50-100 µL per depot) of the fibroblast/collagen suspension were injected into the submucosa circumferentially at three levels, slightly cranial to, slightly caudal to, and between the levels of the injected myoblasts, to treat atrophy of the urethral submucosa (Mitterberger et al. BJU 2007); and b) Delivery into PFMs—levator ani muscle LAM Indication: Anal/Fecal Incontinence (AI/FI).

Patient population: Patients with bothersome AI/FI and external anal sphincter (EAS) dysfunction/atrophy (diagnosed by digital palpation, anal manometry, endoanal ultrasound); Patients with bothersome AI/FI and pelvic floor muscle (PFM) dysfunction; Vaginally parous women with third degree obstetrical laceration/obstetrical anal sphincter injury (OASI)

Time-frames: 1. at the time of primary diagnosis of bothersome AI/FI and EAS dysfunction; 2. as an adjunct therapy at the time of sacral neuromodulation, sphincteroplasty; 3. after failure to respond to other treatments for AI/FI (e.g. pelvic rehabilitation, sacral neuromodulation, sphincteroplasty); 4. at the time of diagnosis of recurrent bothersome AI/FI; 5. at the time of vaginal delivery complicated by a third degree obstetrical laceration/obstetrical anal sphincter injury (OASI)

Delivery Method: a) Delivery into EAS. Transcutaneous endoscopic approach; Transrectal endoscopic approach; b) Delivery into PFMs—levator ani muscle LAM; Transvaginal approach.

Volume/dose: The amount of the ECM hydrogel provided to a patient will depend on such factors as the amount of tissue to be treated.

Indication: Pelvic floor muscle (PFM) dysfunction.

Patient population: Patients with clinically diagnosed PFM dysfunction (clinical assessment of PFM function and by digital palpation, vaginal manometry, pelvic imaging (levator hiatus changes with squeeze)); Vaginally parous women.

Time-frames: 1. at the time of primary diagnosis of PFM dysfunction; 2. as an adjunct therapy to pelvic rehabilitation; 3. after failure to respond to other treatments for PFM dysfunction (e.g. pelvic rehabilitation); 4. at the time of diagnosis of recurrent PFM dysfunction; 5. at the time of vaginal delivery.

Delivery Method: a) Delivery into PFMs—levator ani muscle (LAM); The levator ani complex includes the puborectalis, pubococcygeus, and iliococcygeus muscles. Transvaginal approach (female patients): injectable hydrogel is drawn up into 1-mL syringes with 22G Yale spinal needles attached. 5 mL of 2% lignocaine gel introduced intravaginally to provide local anesthesia; Patients placed in lithotomy position. The muscles to be injected are located by digital vaginal palpation. The puborectalis is located just distal from the hymenal ring. The needle is held in a near horizontal plane. The vaginal epithelium is pierced just inside the hymenal ring, approximately within the posterior third of the hymenal opening. The needle is directed slightly laterally and posteriorly for approximately 5-40 mm. The pubococcygeus is lateral and proximal to the puborectalis muscle. The operator places his/her index finger on the ischial spine and the thumb on the ishion. A spinal needle is then advanced along the outstretched index finger. The needle pierces through the vaginal epithelium, halfway between the ischial spine and the hymenal ring and is advanced approximately 5-40 mm. The needle is held pointing toward the ipsilateral gluteal region while piercing through the vaginal epithelium. The iliococcygeus is located proximal to the pubococcygeus muscle. The operator places his/her index finger on the ischial spine and the thumb on the ishion. A spinal needle is then advanced along the outstretched index finger. The needle pierces through the vaginal epithelium, ⅔ of the way proximal to the hymenal ring and is advanced approximately 5-10 mm 1-mL aliquots injected into two sites bilaterally within each of the puborectalis, pubococcygeus, and iliococcygeus muscles. (from the study of Botox injection for PFM spasm Jarvis et al. Aust N Z J Obstet Gynaecol. 2004) PFM dysfunction can also occur in males, and the approach would be trasrectal Indication: Pelvic Organ Prolapse (POP).

Patient population: Patients with bothersome POP and pelvic floor muscle (PFM) dysfunction; Vaginally parous women Time-frames: 1. at the time of primary diagnosis of bothersome POP and pelvic floor muscle (PFM) dysfunction; 2. as an adjunct therapy at the time of POP repair; 3. after failure to respond to other treatments for POP (e.g. pelvic rehabilitation, pessary, surgery); 4. at the time of diagnosis of recurrent bothersome POP; 5. at the time of vaginal delivery Delivery Method: a) Delivery into PFMs—levator ani muscle LAM; Transvaginal approach.

Indication: Rectal prolapse (RP).

Patient population: Patients with bothersome RP.

Time-frames: 1. at the time of primary diagnosis of bothersome RP; 2. as an adjunct therapy at the time of RP repair; 3. after failure to respond to other treatments for RP (e.g. pelvic rehabilitation, surgery); 4. at the time of diagnosis of recurrent bothersome RP.

Figure 11A:
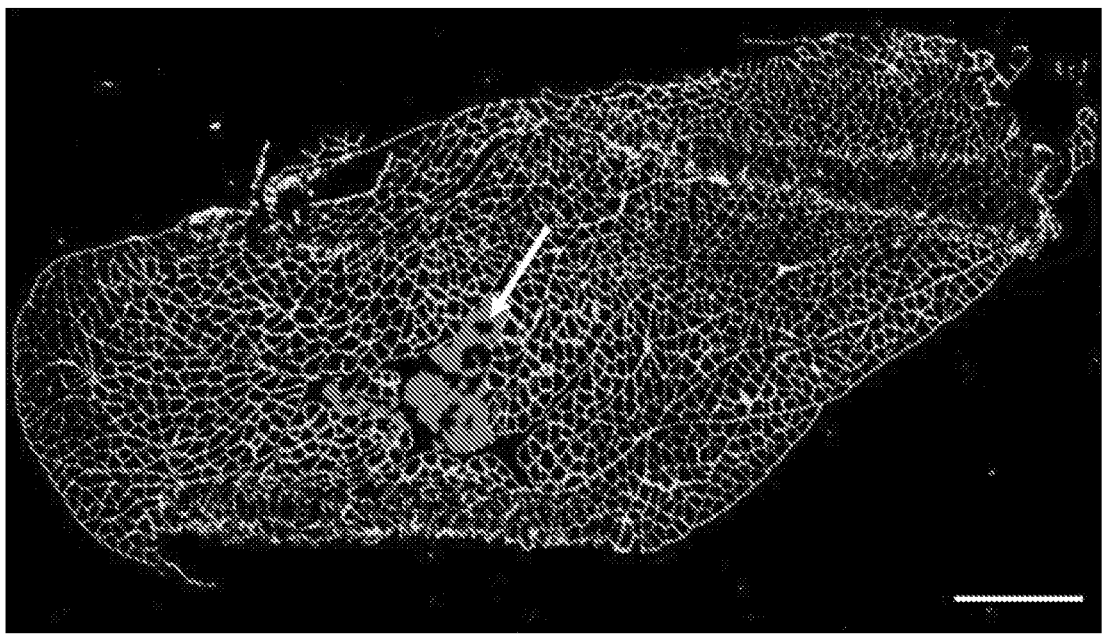
FIGS. 11A-11B illustrate skeletal muscle matrix delivery and gelation in rat pelvic floor.
Figure 11B:
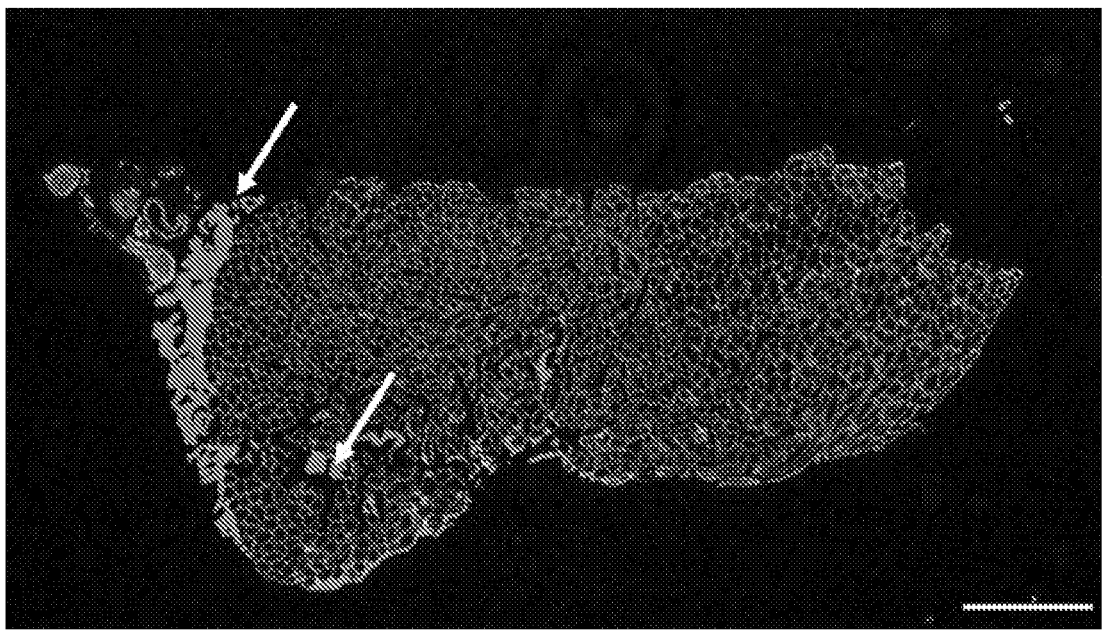

Delivery Method: a) Delivery into EAS and/or PFM; Transrectal endoscopic approach; Transvaginal approach In addition, the skeletal muscle matrix material was demonstrated to form a hydrogel upon injection into rat pelvic floor muscles by ultrasound guidance (FIGS. 11A and 11B).

Figure 12:
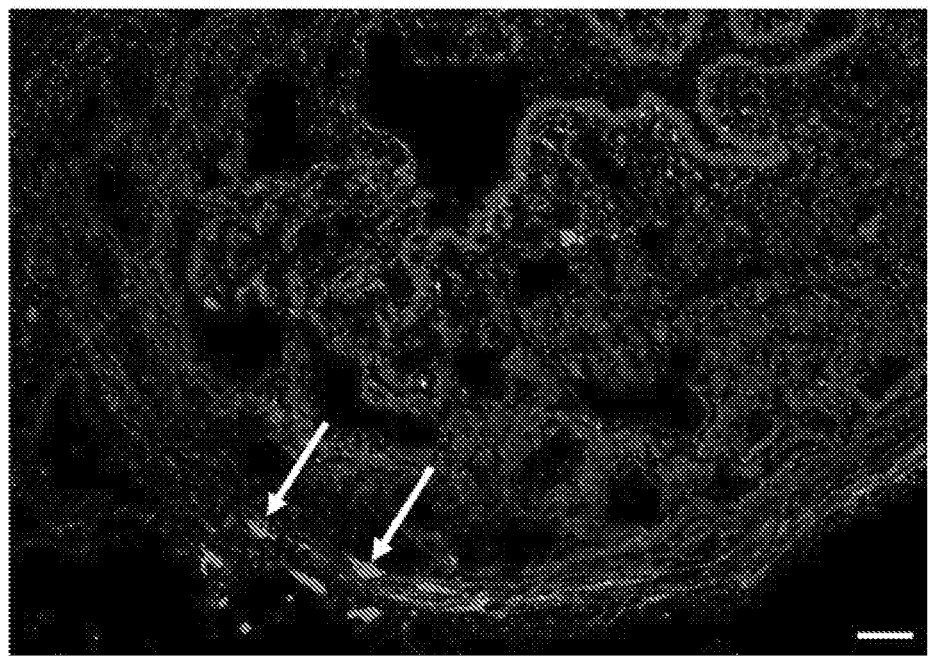
FIG. 12 illustrates skeletal muscle matrix delivery and gelation in rat external urethral sphincter. Arrows denote the gelled white matrix prelabeled with Alexa Fluor 568. Green (laminin), Blue (cell nuclei). Scale bar at 100 µm.
Figure 13A:
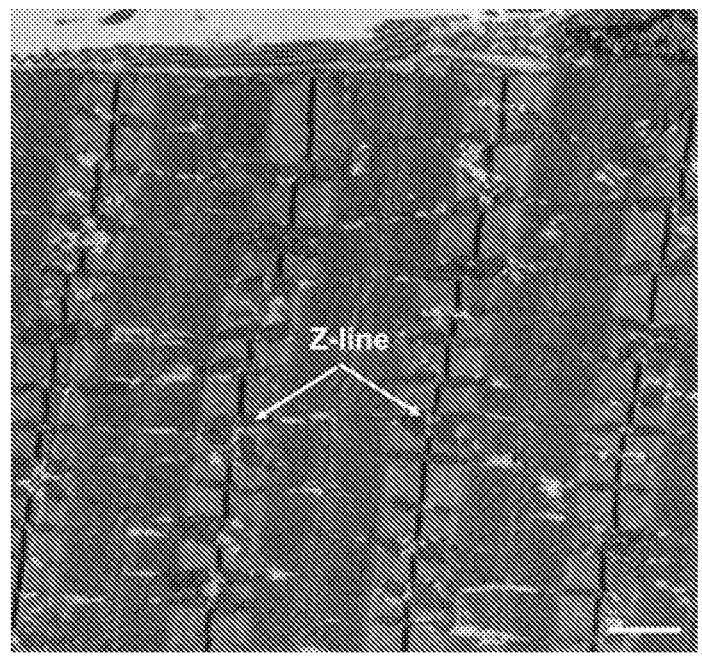
FIGS. 13A-13B illustrate transmission electron microscopy images of external urethral sphincter longitudinal sections.
Figure 13B:
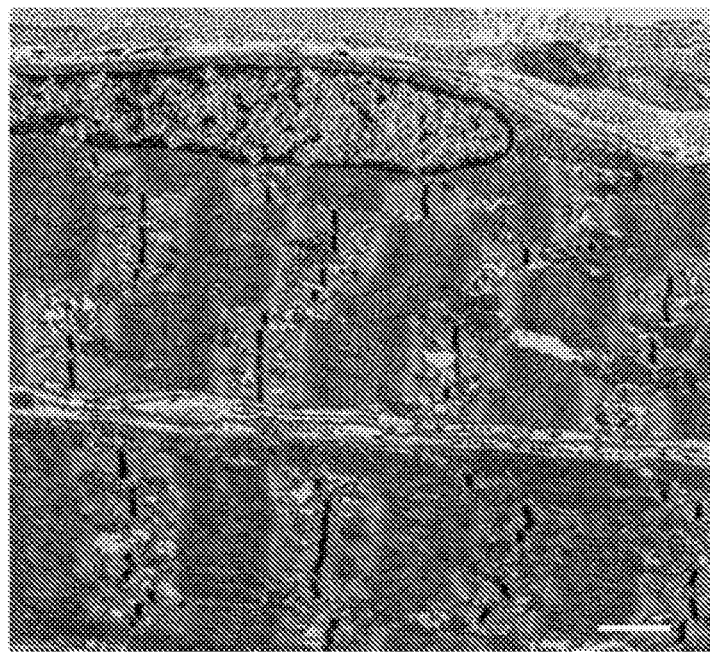
Figure 14A:
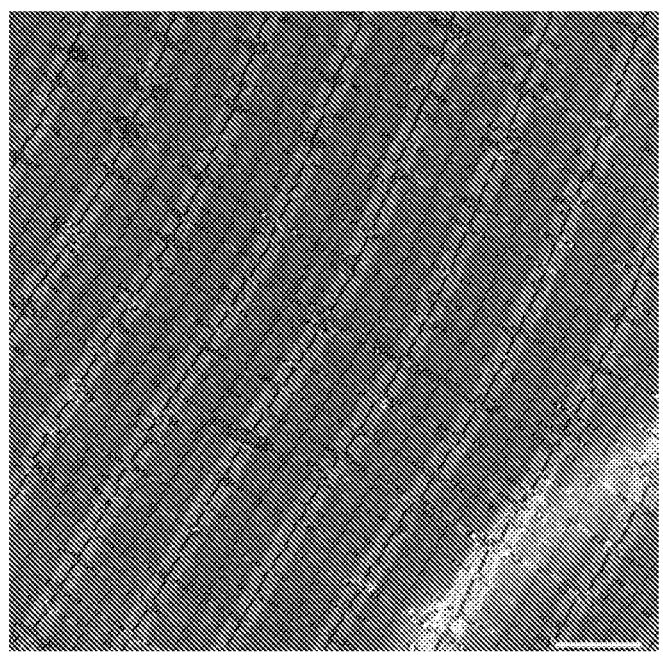
FIGS. 14A-14B illustrate transmission electron microscopy images of pubococcygeus longitudinal sections.
Figure 14B:
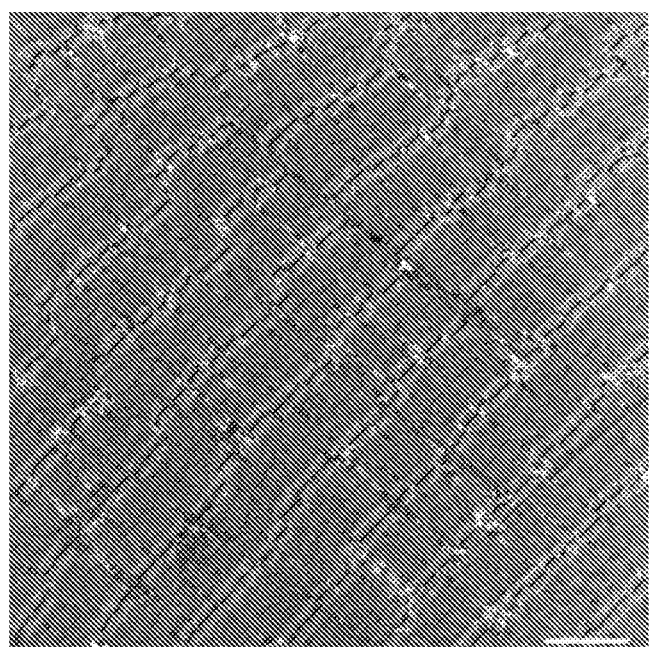

The skeletal muscle matrix material was demonstrated to form a hydrogel upon injection into rat external urethral sphincter by ultrasound guidance (FIG. 12).

Example 8

Focal skeletal muscle atrophy and degeneration: Dysfunction of striated muscles, which include the rotator cuff muscles (supraspinatus, infraspinatus, teres minor, subcapularis), hip abductor muscle (gluteus medius, gluteus minimus, gluteus maximus, and short external rotators), foot and ankle muscles (tibialis posterior, gastrocnemius, soleus), lumbar spine muscles (multifidus, erector spinae), and knee extensor muscles (quadriceps), all suffer from fatty atrophy and muscle degeneration as a consequence of chronic joint disease and other neuromuscular pathologies. This loss of muscle interferes with muscle and joint function, which negatively impacts quality of life.

Indication: Shoulder, hip, foot and ankle, lumbar spine, and knee degenerative joint and tendon diseases, which are associated with focal muscle atrophy and degeneration.

Patient population: Patients with Tendinopathy and/or tendon rupture, Patients with Osteoarthritis, Patients with Rheumatoid arthritis, Patients with Low Back Pain.

Time-frames: 1. at the time of primary diagnosi; 2. as an adjunct therapy at the time of surgical repair of joint or tendon tissues; 3. after failure to respond to other treatments for muscle hypertrophy; 4. at the time of diagnosis of recurrent bothersome joint disease.

Delivery Method: Delivery into striated muscle percutaneously (needle and syringe); Delivery into striated muscle arthroscopically (needle and syringe through an arthroscopic portal); Delivery into striated muscle during open arthrotomy (needle and syringe through an open surgical wound directly into muscle).

Amount of injectate: Approximately 10-50% of muscle volume.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

1. Alev C, Ii M, Asahara T (2011) Endothelial progenitor cells: a novel tool for the therapy of ischemic diseases. Antioxid Redox Signal 15: 949-965.
2. Bach A D, Arkudas A, Tjiawi J, Polykandriotis E, Kneser U, Horch R E, Beier J P (2006) A new approach to tissue engineering of vascularized skeletal muscle. J Cell Mol Med 10: 716-726.
3. Badylak S F (2007) The extracellular matrix as a biologic scaffold material. Biomaterials 28: 3587-3593.
4. Badylak S F, Freytes D O, Gilbert T W (2009) Extracellular matrix as a biological scaffold material: Structure and function. Acta Biomater 5: 1-13.
5. Badylak S F, Gilbert T W (2008) Immune response to biologic scaffold materials. Semin Immunol 20: 109-116.
6. Badylak S F, Park K, Peppas N, McCabe G, Yoder M (2001) Marrow-derived cells populate scaffolds composed of xenogeneic extracellular matrix. Exp Hematol 29: 1310-1318.
7. Banker G, Goslin K (1998) Culturing Nerve Cells. The MIT Press.
8. Beattie A J, Gilbert T W, Guyot J P, Yates A J, Badylak S F (2008) Chemoattraction of Progenitor Cells by Remodeling Extracellular Matrix Scaffolds. Tissue Eng Part A 15: 1119-1125.
9. Belch J J, Topol E J, Agnelli G, Bertrand M, Califf R M, Clement D L, Creager M A, Easton J D, Gavin J R, 3rd, Greenland P, Hankey G, Hanrath P, Hirsch A T, Meyer J, Smith S C, Sullivan F, Weber M A (2003) Critical issues in peripheral arterial disease detection and management: a call to action. Arch Intern Med 163: 884-892.
10. Bhang S H, Kim J H, Yang H S, La W G, Lee T J, Kim G H, Kim H A, Lee M, Kim B S (2011) Combined gene therapy with hypoxia-inducible factor-1alpha and heme oxygenase-1 for therapeutic angiogenesis. Tissue engineering. Part A 17: 915-926.
11. Bruey J M, Kantarjian H, Ma W, Estrov Z, Yeh C, Donahue A, Sanders H, O'Brien S, Keating M, Albitar M (2010) Circulating Ki-67 index in plasma as a biomarker and prognostic indicator in chronic lymphocytic leukemia. Leuk Res 34: 1320-1324.
12. Chan Y C, Cheng S W (2011) Drug-eluting stents and balloons in peripheral arterial disease: evidence so far. Int J Clin Pract 65: 664-668.
13. Christman K L, Vardanian A J, Fang Q, Sievers R E, Fok H H, Lee R J (2004) Injectable fibrin scaffold improves cell transplant survival, reduces infarct expansion, and induces neovasculature formation in ischemic myocardium. J Am Coll Cardiol 44: 654-660.
14. Cooper R N, Tajbakhsh S, Mouly V, Cossu G, Buckingham M, Butler-Browne G S (1999) In vivo satellite cell activation via Myf5 and MyoD in regenerating mouse skeletal muscle. J Cell Sci 112 (Pt 17): 2895-2901.
15. Crapo P M, Gilbert T W, Badylak S F (2011) An overview of tissue and whole organ decellularization processes. Biomaterials 32: 3233-3243.
16. Dattilo P B, Casserly I P (2011) Critical limb ischemia: endovascular strategies for limb salvage. Frog Cardiovasc Dis 54: 47-60.
17. DeQuach J A, Mezzano V, Miglani A, Lange S, Keller G M, Sheikh F, Christman K L (2010) Simple and high yielding method for preparing tissue specific extracellular matrix coatings for cell culture. PLoS One 5: e13039.
18. Diniz G, Aktas S, Turedi A, Temir G, Ortac R, Vergin C (2011) Telomerase reverse transcriptase catalytic subunit expression and proliferation index in Wilms tumor. Tumour Biol 32: 761-767.
19. Doi K, Ikeda T, Marui A, Kushibiki T, Arai Y, Hirose K, Soga Y, Iwakura A, Ueyama K, Yamahara K, Itoh H, Nishimura K, Tabata Y, Komeda M (2007) Enhanced angiogenesis by gelatin hydrogels incorporating basic fibroblast growth factor in rabbit model of hind limb ischemia. Heart Vessels 22: 104-108.
20. Fadini G P, Agostini C, Avogaro A (2010) Autologous stem cell therapy for peripheral arterial disease meta-analysis and systematic review of the literature. Atherosclerosis 209: 10-17.
21. Gilbert T W, Sellaro T L, Badylak S F (2006) Decellularization of tissues and organs. Biomaterials 27: 3675-3683.
22. Gupta R, Losordo D W (2011) Cell therapy for critical limb ischemia: moving forward one step at a time. Circ Cardiovasc Intery 4: 2-5.
23. Hidestrand M, Richards-Malcolm S, Gurley C M, Nolen G, Grimes B, Waterstrat A, Zant G V, Peterson C A (2008) Sca-1-expressing nonmyogenic cells contribute to fibrosis in aged skeletal muscle. J Gerontol A Biol Sci Med Sci 63: 566-579.
24. Jay S M, Shepherd B R, Bertram J P, Pober J S, Saltzman W M (2008) Engineering of multifunctional gels integrating highly efficient growth factor delivery with endothelial cell transplantation. Faseb J 22: 2949-2956.
25. Jeon O, Krebs M, Alsberg E (2011) Controlled and sustained gene delivery from injectable, porous PLGA scaffolds. J Biomed Mater Res A 98: 72-79.
26. Kanisicak O, Mendez J J, Yamamoto S, Yamamoto M, Goldhamer D J (2009) Progenitors of skeletal muscle satellite cells express the muscle determination gene, MyoD. Developmental biology 332: 131-141.
27. Kawamoto A, Katayama M, Handa N, Kinoshita M, Takano H, Horii M, Sadamoto K, Yokoyama A, Yamanaka T, Onodera R, Kuroda A, Baba R, Kaneko Y, Tsukie T, Kurimoto Y, Okada Y, Kihara Y, Morioka S, Fukushima M, Asahara T (2009) Intramuscular transplantation of G-CSF-mobilized CD34(+) cells in patients with critical limb ischemia: a phase I/IIa, multicenter, single-blinded, dose-escalation clinical trial. Stem Cells 27: 2857-2864.
28. Kong H J, Kim E S, Huang Y C, Mooney D J (2008) Design of biodegradable hydrogel for the local and sustained delivery of angiogenic plasmid DNA. Pharm Res 25: 1230-1238.
29. Koyama H, Raines E W, Bornfeldt K E, Roberts J M, Ross R (1996) Fibrillar collagen inhibits arterial smooth muscle proliferation through regulation of Cdk2 inhibitors. Cell 87: 1069-1078.
30. Kuraitis D, Zhang P, Zhang Y, Padavan D T, McEwan K, Sofrenovic T, McKee D, Zhang J, Griffith M, Cao X, Musaro A, Ruel M, Suuronen E J (2011) A stromal cell-derived factor-1 releasing matrix enhances the progenitor cell response and blood vessel growth in ischaemic skeletal muscle. Eur Cell Mater 22: 109-123.
31. Lawall H, Bramlage P, Amann B (2010) Stem cell and progenitor cell therapy in peripheral artery disease. A critical appraisal. Thromb Haemost 103: 696-709.
32. Layman H, Rahnemai-Azar A A, Pham S M, Tsechpenakis G, Andreopoulos F M (2011) Synergistic angiogenic effect of codelivering fibroblast growth factor 2 and granulocyte-colony stimulating factor from fibrin scaffolds and bone marrow transplantation in critical limb ischemia. Tissue Eng Part A 17: 243-254.
33. Layman H, Spiga M G, Brooks T, Pham S, Webster K A, Andreopoulos F M (2007) The effect of the controlled release of basic fibroblast growth factor from ionic gelatin-based hydrogels on angiogenesis in a murine critical limb ischemic model. Biomaterials 28: 2646-2654.
34. Lee J, Bhang S H, Park H, Kim B S, Lee K Y (2010) Active blood vessel formation in the ischemic hindlimb mouse model using a microsphere/hydrogel combination system. Pharm Res 27: 767-774.
35. Lee J Y, Qu-Petersen Z, Cao B, Kimura S, Jankowski R, Cummins J, Usas A, Gates C, Robbins P, Wernig A, Huard J (2000) Clonal isolation of muscle-derived cells capable of enhancing muscle regeneration and bone healing. J Cell Biol 150: 1085-1100.
36. Li F, Li W, Johnson S, Ingram D, Yoder M, Badylak S (2004) Low-molecular-weight peptides derived from extracellular matrix as chemoattractants for primary endothelial cells. Endothelium 11: 199-206.
37. Lutolf M P, Hubbell J A (2005) Synthetic biomaterials as instructive extracellular microenvironments for morphogenesis in tissue engineering. Nat Biotechnol 23: 47-55.
38. Manzi M, Palena L, Cester G (2011) Endovascular techniques for limb salvage in diabetics with crural and pedal disease. J Cardiovasc Surg (Torino) 52: 485-492.
39. Megeney L A, Kablar B, Garrett K, Anderson J E, Rudnicki M A (1996) MyoD is required for myogenic stem cell function in adult skeletal muscle. Genes Dev 10: 1173-1183.
40. Menasché P (2010) Cell therapy for peripheral arterial disease. Curr Opin Mol Ther 12: 538-545.
41. Merritt E K, Hammers D W, Tierney M, Suggs L J, Walters T J, Farrar R P Functional assessment of skeletal muscle regeneration utilizing homologous extracellular matrix as scaffolding. Tissue Eng Part A 16: 1395-1405.
42. Numata S, Fujisato T, Niwaya K, Ishibashi-Ueda H, Nakatani T, Kitamura S (2004) Immunological and histological evaluation of decellularized allograft in a pig model: comparison with cryopreserved allograft. J Heart Valve Dis 13: 984-990.
43. Ott H C, Matthiesen T S, Goh S K, Black L D, Kren S M, Netoff T I, Taylor D A (2008) Perfusion-decellularized matrix: using nature's platform to engineer a bioartificial heart. Nat Med 14: 213-221.
44. Reing J E, Zhang L, Myers-Irvin J, Cordero K E, Freytes D O, Heber-Katz E, Bedelbaeva K, McIntosh D, Dewilde A, Braunhut S J, Badylak S F (2009) Degradation products of extracellular matrix affect cell migration and proliferation. Tissue Eng Part A 15: 605-614.
45. Rhudy R W, McPherson J M (1988) Influence of the extracellular matrix on the proliferative response of human skin fibroblasts to serum and purified platelet-derived growth factor. J Cell Physiol 137: 185-191.
46. Rieder E, Nigisch A, Dekan B, Kasimir M T, Muhlbacher F, Wolner E, Simon P, Weigel G (2006) Granulocyte-based immune response against decellularized or glutaraldehyde cross-linked vascular tissue. Biomaterials 27: 5634-5642.
47. Ruvinov E, Leor J, Cohen S (2010) The effects of controlled HGF delivery from an affinity-binding alginate biomaterial on angiogenesis and blood perfusion in a hindlimb ischemia model. Biomaterials 31: 4573-4582.
48. Scholzen T, Gerdes J (2000) The Ki-67 protein: from the known and the unknown. J Cell Physiol 182: 311-322.
49. Seif-Naraghi S B, Salvatore M A, Schup-Magoffin P J, Hu D P, Christman K L (2010) Design and characterization of an injectable pericardial matrix gel: a potentially autologous scaffold for cardiac tissue engineering. Tissue Eng Part A 16: 2017-2027.
50. Silva E A, Mooney D J (2007) Spatiotemporal control of vascular endothelial growth factor delivery from injectable hydrogels enhances angiogenesis. J Thromb Haemost 5: 590-598.
51. Singelyn J M, DeQuach J A, Seif-Naraghi S B, Littlefield R B, Schup-Magoffin P J, Christman K L (2009) Naturally derived myocardial matrix as an injectable scaffold for cardiac tissue engineering. Biomaterials 30: 5409-5416.
52. Singelyn J M, Sundaramurthy P, Johnson T D, Schup-Magoffin P J, Hu D P, Faulk D M, Wang J, Mayle K M, Bartels K, Salvatore M, Kinsey A M, Demaria A N, Dib N, Christman K L (2012) Catheter-deliverable hydrogel derived from decellularized ventricular extracellular matrix increases endogenous cardiomyocytes and preserves cardiac function post-myocardial infarction. Journal of the American College of Cardiology 59: 751-763.
53. Sprengers R W, Lips D J, Moll F L, Verhaar M C (2008) Progenitor cell therapy in patients with critical limb ischemia without surgical options. Ann Surg 247: 411-420.
54. Stansby G, Williams R (2011) Angioplasty for treatment of isolated below-the-knee arterial stenosis in patients with critical limb ischemia. Angiology 62: 357-358.
55. Sundararaghavan H G, Metter R B, Burdick J A (2010) Electrospun fibrous scaffolds with multiscale and photopatterned porosity. Macromol Biosci 10: 265-270.
56. Tongers J, Roncalli J G, Losordo D W (2008) Therapeutic angiogenesis for critical limb ischemia: microvascular therapies coming of age. Circulation 118: 9-16.
57. Uriel S, Labay E, Francis-Sedlak M, Moya M L, Weichselbaum R R, Ervin N, Cankova Z, Brey E M (2009) Extraction and assembly of tissue-derived gels for cell culture and tissue engineering. Tissue Eng Part C Methods 15: 309-321.
58. Uygun B E, Soto-Gutierrez A, Yagi H, Izamis M L, Guzzardi M A, Shulman C, Milwid J, Kobayashi N, Tilles A, Berthiaume F, Hertl M, Nahmias Y, Yarmush M L, Uygun K (2010) Organ reengineering through development of a transplantable recellularized liver graft using decellularized liver matrix. Nat Med 16: 814-820.
59. Valentin J E, Turner N J, Gilbert T W, Badylak S F (2010) Functional skeletal muscle formation with a biologic scaffold. Biomaterials 31: 7475-7484.
60. Wada M R, Inagawa-Ogashiwa M, Shimizu S, Yasumoto S, Hashimoto N (2002) Generation of different fates from multipotent muscle stem cells. Development 129: 2987-2995.
61. Webber M J, Tongers J, Newcomb C J, Marquardt K T, Bauersachs J, Losordo D W, Stupp S I (2011) Supramolecular nanostructures that mimic VEGF as a strategy for ischemic tissue repair. Proceedings of the National Academy of Sciences of the United States of America 108: 13438-13443.

62. Wolf M T, Daly K A, Reing J E, Badylak S F (2012) Biologic scaffold composed of skeletal muscle extracellular matrix. Biomaterials 33: 2916-2925.
63. Yamamoto D L, Csikasz R I, Li Y, Sharma G, Hjort K, Karlsson R, Bengtsson T (2008) Myotube formation on micro-patterned glass: intracellular organization and protein distribution in C2C12 skeletal muscle cells. J Histochem Cytochem 56: 881-892.
64. Young D A, Ibrahim D O, Hu D, Christman K L (2011) Injectable hydrogel scaffold from decellularized human lipoaspirate. Acta Biomater 7: 1040-1049.
65. Zantop T, Gilbert T W, Yoder M C, Badylak S F (2006) Extracellular matrix scaffolds are repopulated by bone marrow-derived cells in a mouse model of achilles tendon reconstruction. J Orthop Res 24: 1299-1309.

The invention claimed is:

1. A method comprising administering by intramuscular injection in a subject with muscle degeneration an effective amount of a composition comprising decellularized extracellular matrix derived from skeletal muscle tissue, wherein the muscle degeneration in the subject is due to a condition selected from the group consisting of pelvic floor muscle (PFM) fibrosis, pelvic floor disorders (PFD), urinary incontinence (UI), fecal incontinence (FI), pelvic organ prolapse (POP), dysfunction of pelvic striated muscles, external urethral sphincteric (EUS) muscles, external anal sphincteric (EAS) muscles, rectal prolapse (RP), stress urinary incontinence (SUI), and mixed urinary incontinence (MUI).

2. The method of claim 1, wherein said composition is coated on an implant.

3. The method of claim 1, wherein said composition is delivered as a liquid or a powder.

4. The method of claim 3, wherein said composition transitions to a gel form after delivery.

5. The method of claim 1, wherein said composition degrades within one to three months following injection or implantation.

6. The method of claim 1, wherein injection or implantation of said composition repairs damage to skeletal muscle tissue sustained by said subject.

7. The method of claim 1, wherein injection or implantation of said composition repairs damage caused by acute sarcomere hyperelongation and myofibrillar disruption in said subject.

8. The method of claim 1, wherein said effective amount is an amount that increases blood flow, increases muscle mass, or induces new vascular formation in the area of the injection or implantation of the subject.

9. The method of claim 1, wherein the effective amount is effective for treating a birth trauma and consequent dysfunction of pelvic floor musculature.

* * * * *